United States Patent [19]
Wolf

[11] Patent Number: 5,809,997
[45] Date of Patent: Sep. 22, 1998

[54] ELECTRONIC MEDICATION CHRONOLOG DEVICE

[75] Inventor: James L. Wolf, Littleton, Colo.

[73] Assignee: Medtrac Technologies, Inc., Lakewood, Colo.

[21] Appl. No.: 541,492

[22] Filed: Oct. 10, 1995

Related U.S. Application Data

[63] Continuation-in-part of Ser. No. 444,835, May 18, 1995, abandoned.

[51] Int. Cl.$^6$ .................. A61M 11/00; A61M 16/00; A62B 9/00; G08B 3/00
[52] U.S. Cl. .................. 128/200.23; 128/202.22; 128/205.23
[58] Field of Search .................. 128/200.14, 200.23, 128/202.22, 205.23, 203.12

[56] References Cited

U.S. PATENT DOCUMENTS

| 5,167,506 | 12/1992 | Kilis et al. | 128/200.23 |
| 5,284,133 | 2/1994 | Burns et al. | 128/200.23 |
| 5,333,106 | 7/1994 | Lanpher et al. | 128/200.23 |
| 5,363,842 | 11/1994 | Mishelevich et al. | 128/200.23 |

FOREIGN PATENT DOCUMENTS

| 9106334 | 5/1991 | WIPO | 128/200.23 |
| 9207599 | 5/1992 | WIPO | 128/203.12 |
| 9217231 | 10/1992 | WIPO | 128/200.23 |
| 9312823 | 7/1993 | WIPO | 128/203.12 |

Primary Examiner—Kimberly L. Asher
Attorney, Agent, or Firm—Sheridan Ross P.C.

[57] ABSTRACT

An electronic medication chronolog device adapted for attachment to various shapes and sizes of conventional pressurized inhalant packages. The packages include in common an actuator housing with one end having a mouthpiece and an opposite end having an opening for receiving a vial/canister therein. The vial/canister having a valve stem used for dispensing a prescribed dosage of medication inhalant in an aerosol chamber inside the actuator housing. The aerosol chamber is disposed next to an outlet of the mouthpiece for dispensing the medication therethrough. The chronolog device includes computing and recording equipment with audio and visual display mounted in a chronolog housing. The chronolog housing is adapted for attachment to the actuator housing. A strain gauge sensing arm is attached to the computing equipment and extends through a hole in a side of the actuator housing for engaging a portion of the vial/canister next to the valve stem. The sensing arm senses and signals the computing equipment when the valve stem of the vial/canister is properly compressed for release of medication. Also, the sensing arm senses and signals the computing equipment when the vial/canister is engaged and disengaged inside the actuator housing Further, a fast response thermistor is connected to the computing equipment and disposed between the hole in the side of the actuator housing and an opening in the chronolog housing. The thermistor senses and signals each occurrence and amount of inhale air flow and exhale air flow in the actuator housing.

7 Claims, 12 Drawing Sheets

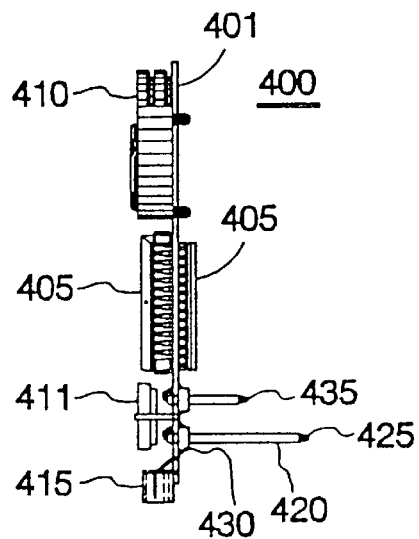
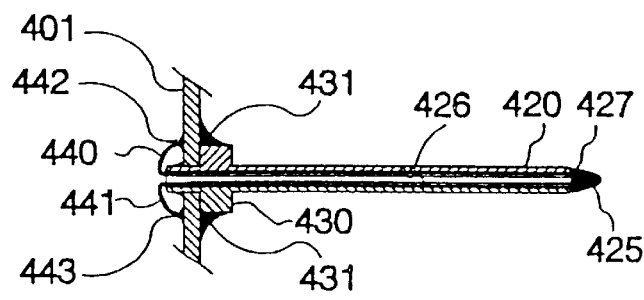
FIGURE 4
FIGURE 4a
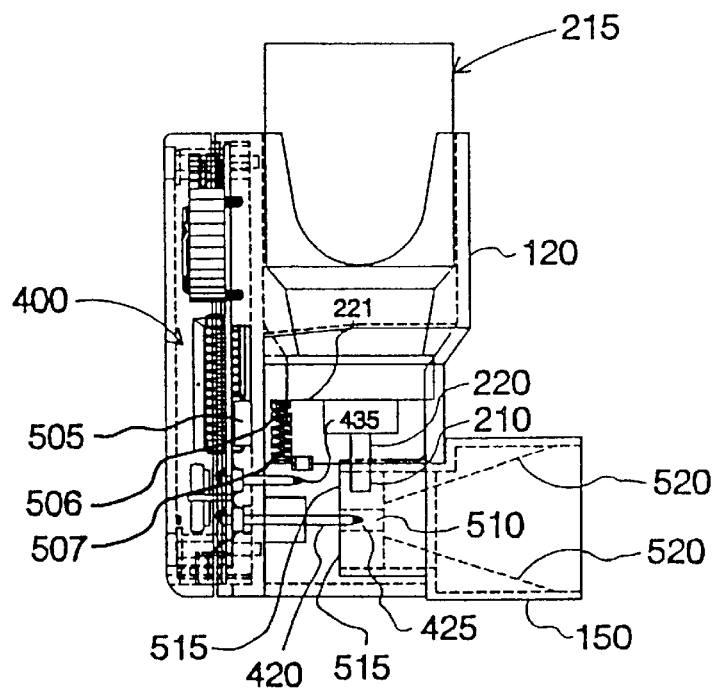
FIGURE 5

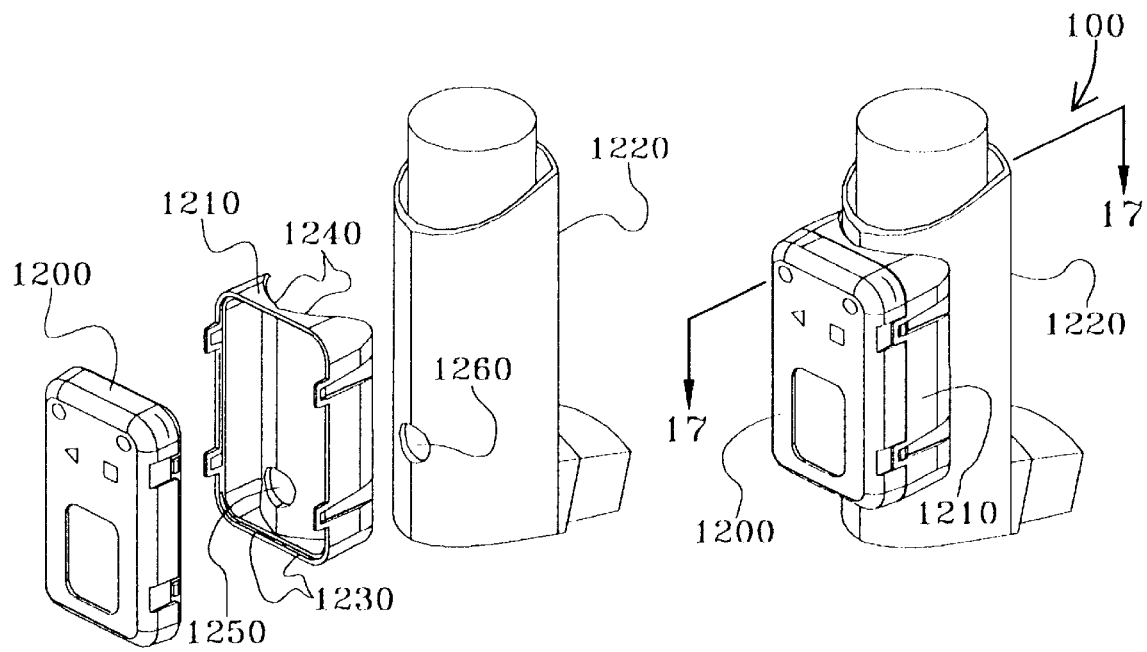
FIRURE 12    FIGURE 13
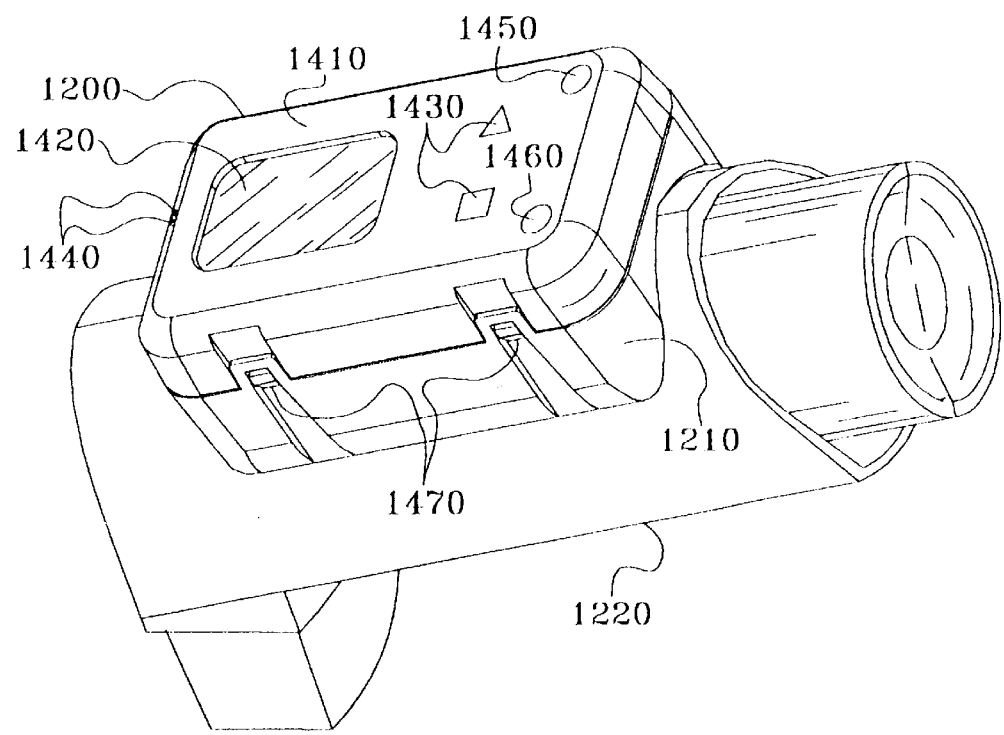
FIGURE 14

ELECTRONIC MEDICATION CHRONOLOG DEVICE

RELATED APPLICATION

This application is a continuation-in-part of applicant's continuation application Ser. No. 08/444,835, entitled "MEDICATION INHALER DEVICE", filled on May 18, 1995, now abandoned.

1. Field of the Invention

The present invention relates, in general, to the field of prescribed medication monitoring and, more particularly, to an electronic device which attaches (piggyback) and is adaptable to any metered dose inhalant commercial vial/actuator combination, as an accessory, for the purpose of sensing the patient/user inhalation of medicated drug to chronologically record performance and provide feedback as a means of compliance control and better patient care with wireless communications for remote analysis and management of treatment.

2. Statement of the Problem

The medical drug industry has come a long way in developing "miracle" wonder drugs in the last century. Patients benefit, in many cases, to complete recovery from diseases that were once fatal when contracted. With today's sophisticated super drugs, one expects success with such treatment.

However, success is greatly determined by the diligence of medication dispensing at prescribed dosages and properly administered in timely manner. When patients are in hospitals, diligent dispensing of medication is certainly practiced, but even in hospitals there is no positive log of such medication dispensing. In out-patients, the diligence of following the prescribed schedules is dramatically diminished. Often the patient or family member is forgetful and exact times of medication are missed, totally forgotten or proper dosages are erroneous.

Unfortunately, patients are not getting the full benefit of prescribed drugs because exact adherence to critical dispensing schedules and dosage amounts are not being reliably accounted for. Doctors are, at best, guessing the patient has followed mediation instructions completely, and are making vital decisions accordingly.

Patient monitoring, with respect to compliance to prescribed medication, is of significant concern to health care and pharmaceutical research institutions. Patients, and/or their care providers, are often confused by physician's instructions, schedules, dosages, etc. in the administration of medication. This is especially disconcerting when a medication dosage is meant to be on a sliding scale dependent on how the patient is feeling at the time medication is to be dispensed.

Physicians and drug researchers often must take lengthy patient interviews and pore through logs, journals, and handwritten diaries to ascertain whether medication has been taken appropriately, and as prescribed. With even the best and diligent patient cooperation, physicians and researchers can not fully rely on this form of feedback. ("Failure to adhere to medication regimens occurs in 25 to 50% of patients. This may lead to apparent treatment failure or apparent lack of effectiveness in clinical trials." Rand C. S., et.al., American Review of Respiratory Disease, 1992)

The basis of managed patient care is the compliance of the patient with the therapeutic regimen prescribed by the physician. Within this premise are three scenarios which the patient may follow: a) the patient follows the regimen and the symptoms of the disease are mediated, b) the patient follows the regimen and the symptoms are not mediated, suggesting a different regimen is required, or c) the patient does not follow the regimen and no relief ensues. One of the most discomforting facts about this situation is that the elderly, or the very sick, are the ones on the wrong side of the statistics: the groups many medications are intended to help. ("About 1.5 billion prescriptions are written each year. The prescribed medications may provide great benefits for patients, yet these benefits may be lost if patients do not use the medications properly . . . . It is estimated that 55% of the elderly do not comply with their medication regimens." Kessler David A., Commissioner, Food and Drug Administration, editorial, New England Journal of Medicine, Dec. 5, 1991)

Patient noncompliance with therapeutic treatment regimens is perhaps the most difficult issue facing medical practice today. Not only does poor compliance reduce, or negate, the value of treatment to patients, but it is also a crucial factor in analyzing the results of clinical trials in the drug development research conducted by pharmaceutical companies. The safety and efficacy of new pharmaceutical products remain in question since the data generated during clinical trials is often based upon flawed reporting practices such as indicated above.

The issue of compliance is critical for both the pharmaceutical development and manufacturing companies, whose discovery-to-market cycle approaches twelve years and four hundred million dollars for each new pharmaceutical entrant into the market, and the physician engaged in therapeutic patient management. A major component of the pharmaceutical respiratory medication development cycle is the clinical trial, engaging several hundred subjects employed to substantiate the safety and efficacy of each new drug. Noncompliance on the part of the trialists (1) increases the number of trialists required to compensate for acknowledged, unmeasured noncompliance, (2) negatively impacts the validity of data generated throughout the clinical study, (3) extends the time frame of the clinical trial study, particularly in the data analysis validation and reporting functions, and (4) significantly increases the total cost of development of new therapeutic pharmaceuticals.

Even with the electronic devices available on the market today, which may "beep" to remind patients to take their medication, or "count" usage or dispensing and the recording of such data, the problems above stated still exist. Despite even the most well meaning intentions of patients and their care providers, prescribed medication goes un-administered, forgotten, under medicated (too little), over medicated (too much) or improperly medicated (dispensed, but not in a correct manner), etc. The feedback the physician or researcher needs to rely on is compromised due to the lack of consistent, reliable information.

Another problem to further complicate the electronic devices mentioned above is that they are expensive dedicated instruments which typically have actuator housing structures incorporated that resemble commercial pharmaceutical actuator manufactured devices. These systems only use the drug vial/canister as is conventionally available inserted into the instrument. The main problem with all these systems is that many drugs are regulated and require exact actuator conformity. That is, there can be no deviation in the actuator structure from the pharmaceutical manufacturer. Any deviation from the original actuator, as is manufactured by the pharmaceutical developer, is considered an interference and may distort the reliability in delivering the drug.

The issue of the exact actuator, which was field tested costing tens of millions of dollars by each of the original drug developer/manufacturers, is of significant consideration in many applications. This is so even in the most faithful reproduction of actuator structures. Physicians, researchers, insurance companies, etc., simply do not want to take a chance (in terms of liability) in possibly altering the delivery of medicated drug through these dedicated electronic instruments with out the same assurance of proper drug delivery as with the commercial actuator provided by the drug manufacturer.

3. Solution to the Problem

The problems set out above are solved by the present invention: an accessory chronolog apparatus which attaches and is adaptable to any commercially available original actuator and vial/canister for medication metered dose inhalant (MDI) dispensing. The apparatus includes a visual display, audible alarms and tactile pushbuttons. The present invention has the capabilities to determine proper dispensing of medication as to being delivered into the patient's mouth, throat and respiratory system and record all usages. Further, the apparatus can communicate wirelessly to conveniently "output" organized patient compliance information and/or receive "input" instructions from a remote physician, researcher or care provider.

The accessory chronolog apparatus of the present invention uniquely interacts with the commercial vial/canister actuator combination such as to not interfere with any functions of the MDI as does all prior art, thus maintaining the original integrity of the pharmaceutical manufactured commercial vial/canister actuator combination, with its ten of millions of dollars of testing and Food and Drug Administration (FDA) authorizations and approvals.

Effective patient management requires an unequivocal means of monitoring patient compliance with the prescribed therapeutic regimen and a means to sense MDI activity without interfering with the original integrity of a pharmaceutical manufactured commercial vial/canister actuator combination. The piggyback, adaptable commercial actuator chronolog apparatus of the present invention addresses all the issues above listed problems and will provide the pharmaceutical development and manufacturing companies a significant cost control advantage, while also providing objective clinical study information superior to the acknowledged inefficient data currently reported and analyzed.

The present invention is not related to improving medication dispensing devices, but rather sets forth a device for attaching to existing medication dispensers to more properly control the behavior which a patient uses the medication dispensing device. It is a portable unit, highly miniaturized to fit within the grip of a closed hand. Doctors can program the desired dosage and schedule into the device along with the patient's name and the prescribed drug. The patient then inserts the prescribed drug in its manufacturer's actuator dispenser package (which has attached "piggyback" to it the apparatus of the present invention). The apparatus shall then remind the patient when to take the medication and determine if the drug was properly "mixed" as recommended. The apparatus logs the exact time and date of each usage, as well as an indication of the appropriate delivery. The patient may change out depleted drug dispenser packages as needed and replace with new ones. The apparatus of the present invention even records this event.

The apparatus can communicate, with no physical connections (wirelessly), to a retrieval device for "up-loading" the recorded events. From this data, a full accountability of prescribed drug usage is listed including the positive determination that the medication was received into the patients mouth, throat and respiratory system. The doctor can now make critical judgment calls based on exact information as to compliance: interval, missed scheduled medications, "strength" of medication, etc.

DISCUSSION OF PRIOR ART

In the prior issued patent entitled "Timed Pill Monitor and Dispenser", U.S. Pat. No. 4,662,537, issued on May 5, 1987 to the present inventor, a medication monitor was disclosed wherein pre-packaged medication "pills" were placed into compartmental chambers on a hand held device for later usage. Such a system is useful for recording the event of each time a chamber was accessed and a pill removed for prescribed medication.

The present invention provides a positive registration that a medicated inhalant has been properly dispensed and logged.

Prior to the filing of this application, the subject inventors conducted a patentability investigation for a system that monitors the administration of prescribed drugs, and provides a chronological report for all activity therewith. The following patents, in addition to the above stated patent, were uncovered in the search:

| Inventor | Reg. No. | Date |
| --- | --- | --- |
| Kehr et al. | 5,200,891 | Apr. 6, 1993 |
| Johnson, IV et al. | 5,133,343 | Jul. 28, 1992 |
| Wood et al. | 5,097,429 | Mar. 17, 1992 |
| Moulding | 5,042,685 | Aug. 27, 1991 |
| Foley | 5,042,467 | Aug. 27, 1991 |
| Moulding | 4,869,352 | Sep. 26, 1989 |
| Behl | 4,473,884 | Sep. 25, 1984 |
| Moulding | 4,460,106 | Jul. 17, 1984 |

The patent issued to Kehr et al (U.S. Pat. No. 5,200,891) pertains to a device having a plurality of compartments, each of which store medication pills and an electrical signaling system to emit medication alert signals. The disclosed signals indicate that medication should be taken, from which compartment, and the quantity. The device of Kehr has a high degree of inter-action between the user and its operation by selecting push-buttons and reading messages on the device display.

In the apparatus of Johnson, IV et al. (U.S. Pat. No. 5,133,343) has a user's mouthpiece housed therein an automatically actuated commercially available and replaceable inhalers for discharging a medicated vapor. The primary objective of Johnson, IV invention is to provide a device for actuating an inhaler in response to inhalation by a user.

In the 1992 patent issued to Wood et al. (U.S. Pat. No. 5,097,429) pertains to a user-programmable microprocessor-based apparatus which acts as a reminder to a medication schedule of events. When a user programs parameters relating to intervals of medication, the device prompts the user by signaling alarm.

The third patent of Moulding (U.S. Pat. No. 5,042,685, Aug. 27, 1991) manages the dispensing of pills. While the second patent of Moulding (U.S. Pat. No. 4,869,352, Sep. 26, 1989) pertains to conforming to the shape and size of pill for dispensing, and Moulding's Jul. 17, 1984 patent (U.S. Pat. No. 4,460,106) concerns the counting of pills being dispensed.

In the Foley patent (U.S. Pat. No. 5,042,467) teaches improved misting of inhaler medication which provides warning by means of sonic signaling if the user inhales too vigorously.

In the 1984 patent issued to Behl (U.S. Pat. No. 4,473,884) sets forth an electronically controlled medication dispenser with a second pharmacy programmer used to program the dispenser. The dispenser includes a plurality of compartments for storage of tablets or pills. Each compartment has associated indicators which activate and are announced audibly, first softly, and then increasingly in magnitude to a programmed time schedule. The user would then open indicated compartment and take the suggested dosage of medication. The pharmacy desktop sized programmer may program the electronic dispenser to optimize the medication schedule with user's personal eating and sleeping habits. Such information is programmed into a non-volatile memory within.

None of the above approaches discloses an accessory device which attaches to any commercially available vial actuator combination. Further none of the above approaches discloses an approach for chronologically recording dispensed medication as to the determination that the drug was positively received into the user's mouth, throat and respiratory system. Many of the devices have push-buttons associated with the apparatus to program schedules that essentially function as a reminder with no positive action that medication has been taken. Others simply "count" device activations. Of the dispensing electronic apparatuses, they pertain to "pill" or "tablet" form of medication that count activation and/or remind the patient. The inhalant related patents provide assistance to the user in the administration of the inhalant medication. Finally, none of the prior art have wireless communications ability and a means to output to, and receive from, the outside world to remotely manage by means of an in home docking station.

SUMMARY OF THE INVENTION

An object of the present invention is an improved accessory chronolog which will mount "piggyback" to conventional, commercially available vial/actuator combinations of dispensing metered dose inhalant devices. The accessory chronolog shall not interfere with, or alter, the original pharmaceutical manufactured vial/actuator combination so as to preserve its original tested and FDA approved performance with respect to the delivery of the medicated inhalant.

Another object of the present invention is an adaptable housing, which shall afford the accessory chronolog apparatus to be economically mounted to any of the pharmaceutical manufactured vial/actuator combinations available, making an improved apparatus which allows the original manufacturer tested and FDA approved actuators fitted for monitoring the user/patient for proper usage and compliance without interfering with, or altering, the delivery of medication. The apparatus, by means of an accelerometer and reed switch generating a mixing detect signal, properly indicates that the pharmaceutical manufacturer's recommendation for pre-mixing the medication has occurred prior to inhalation of said medication. That a strain guage dynamic sensing arm indicated that a vial/canister is received into the commercial actuator and is properly seated into its aerosol chamber and ready for use, and, that it can detect the start and valid actuation of the medication delivery process. That an air flow fast response thermistor can detect the proper inhalation sequence in the medication delivery; as the user/patient inhales through the mouthpiece, a portion of air would enter the air inlet in the housing (of the improved apparatus) passing through an air channel and a hole in the main printed circuit board. As the air passes through the hole in the main-PCB, it is sensed by pass over a very small fast response thermistor and continue through the access hole that is shared with the dynamic sensing arm. This fraction of inhaled air, via the mouthpiece, is representative of the remainder of air drawn into the commercial actuator around the sides of the vial/canister. At any exhalation by the patient, exhaled air would reverse the above indicated path, allowing a fraction out the access hole and through the main-PCB over the thermistor and through the air channel and expelled out the inlet holes.

The generated signals (each may be recorded) will document that a user/patient has complied with all pharmaceutical manufacturer's recommendations as well as the prescribing physician's instructions. This determination results in data indicative that medication has positively been dispensed in the user/patient's mouth, throat and respiratory system after being properly mixed. Any deviation from a correct usage will be detected. Examples of incorrect usage sensed are: medication not mixed enough, vial/canister not properly seated, premature delivery, delayed delivery, not inhaling long enough, not holding breath long enough, inhaling too hard or too fast, or too soft or too slow. These deviations from correct and proper usage result in the medication either landing and dissolving on the back of the throat or on the tongue of the patient instead of being received into the respiratory system where it is intended.

All such events and maneuvers are either displayed on the display panel and/or indicated on the piezo transducer audibly for immediate feedback to the user/patient. Further the events are time-stamped and recorded in the device memory system for retrieval at some later time. The system of the present invention can record for as long as six month, depending on preprogrammed configuration. Still another objective is that there are infrared (IR) transmitting and receiving elements, to wirelessly communicate (short range) with either peripheral support devices or directly to a personal computer for the up-loading of stored memory acquired data. The retrieved information is an exact user/patient "mapping" as to the performance of medication being delivered from the improved accessory apparatus of the present invention.

The present invention takes advantage of the much smaller sized accessory chronolog, making a convenient means to more effectively monitor, instruct, record performance and transfer data to and from the physician/care provider. The disadvantages listed earlier in this disclosure are overcome through the adaptable housing of the improved present invention providing an economical means to measure the original pharmaceutical manufactured vial/actuator combination in MDI dispensing to true and faithful medication compliance.

BRIEF DESCRIPTION OF THE DRAWINGS

The accompanying drawings illustrate complete preferred embodiments of the present invention according to the best modes presently devised for the practical application of the principles thereof, and in which:

FIG. 4 is a side planar view of the electronics assembly and sensing elements of the present invention.

FIG. 4a is a cross-sectional view showing detail of the electronic main sensing element shown in FIG. 4.

FIG. 5 is a side planar illustration showing the device of FIG. 2 and FIG. 4 fully assembled.

DESCRIPTION OF THE DRAWINGS IN THE IMPROVED APPARATUS

Figure 15A:
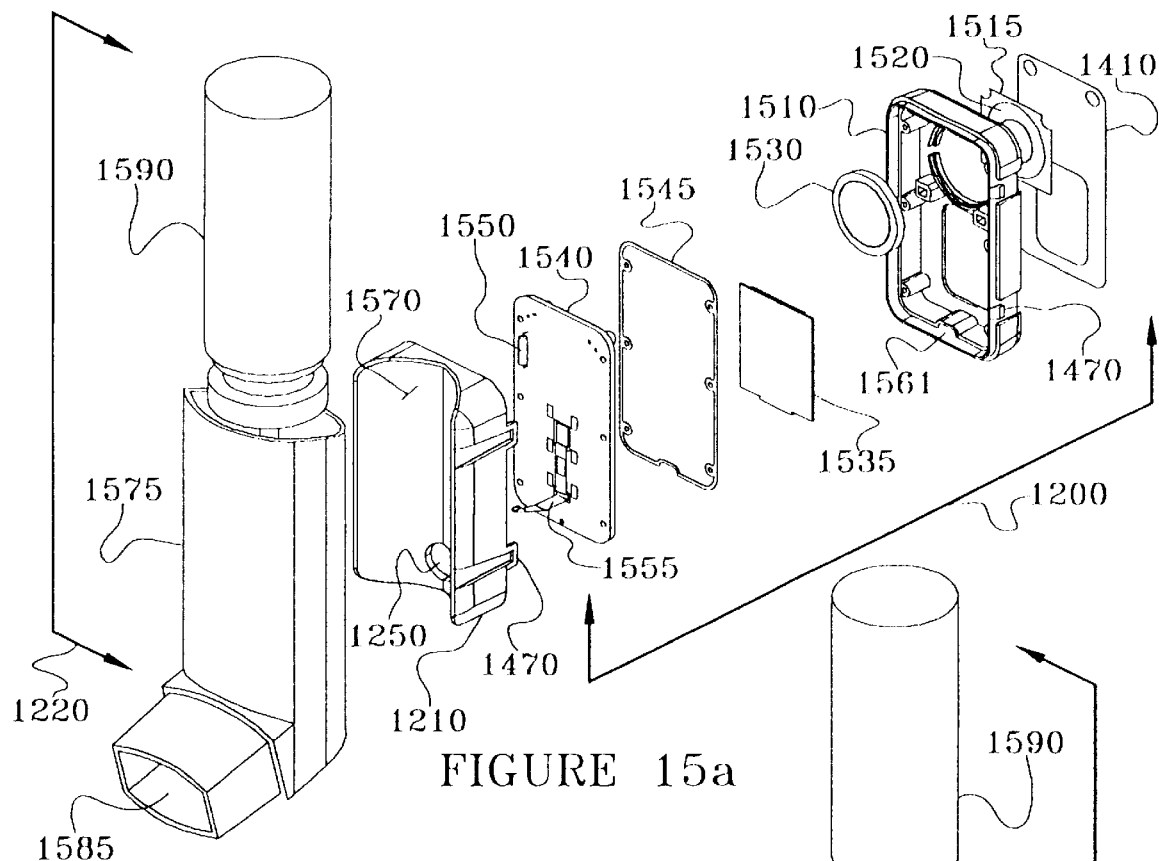
Figure 15B:
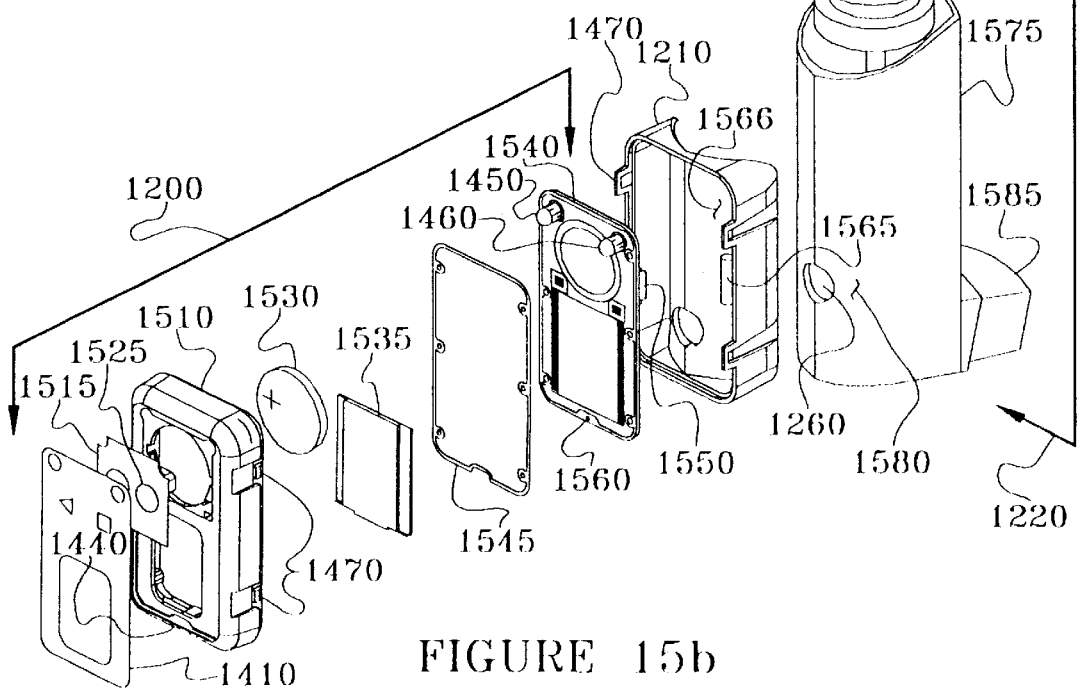
Figure 16:
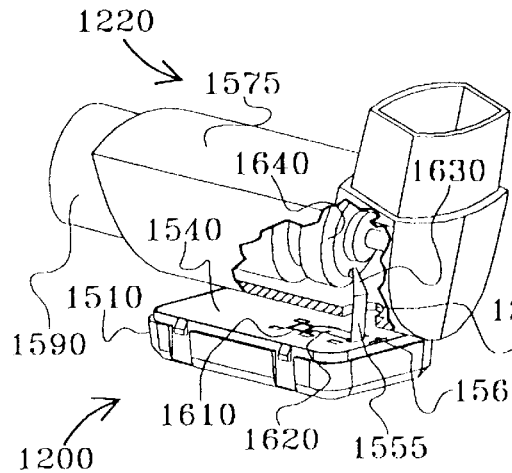
Figure 17A:
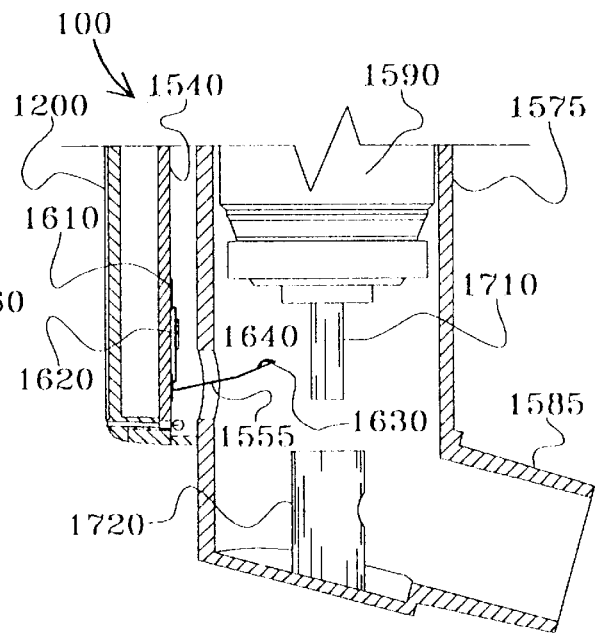
Figure 17B:
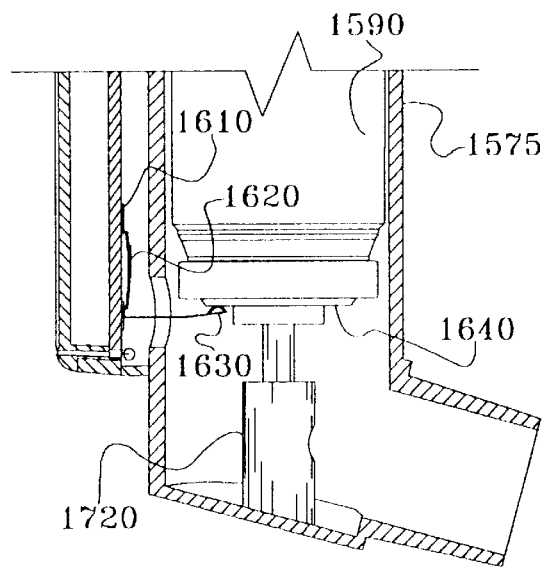
Figure 17C:
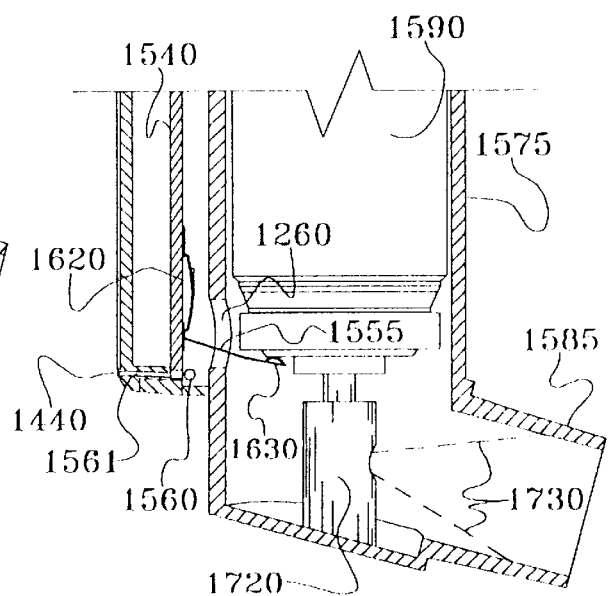
Figure 18A:
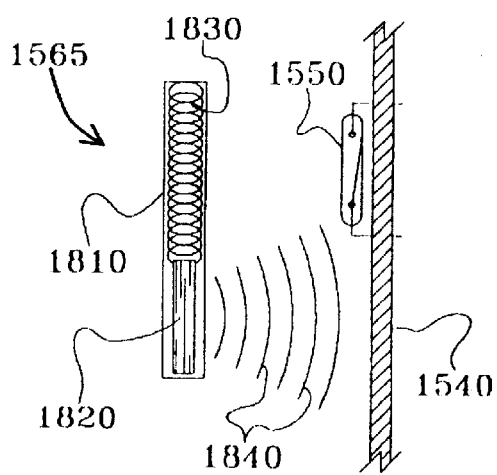
Figure 18B:
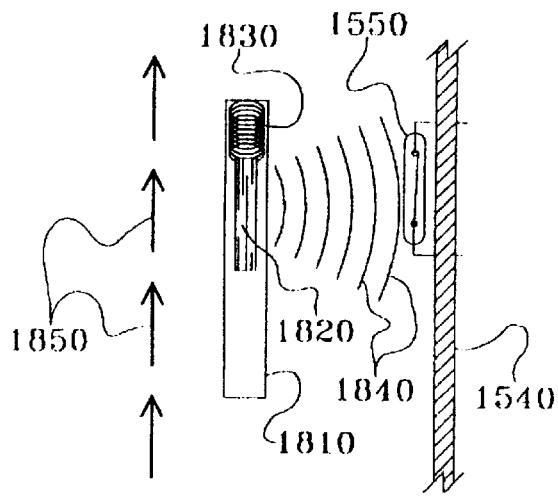
Figure 20:
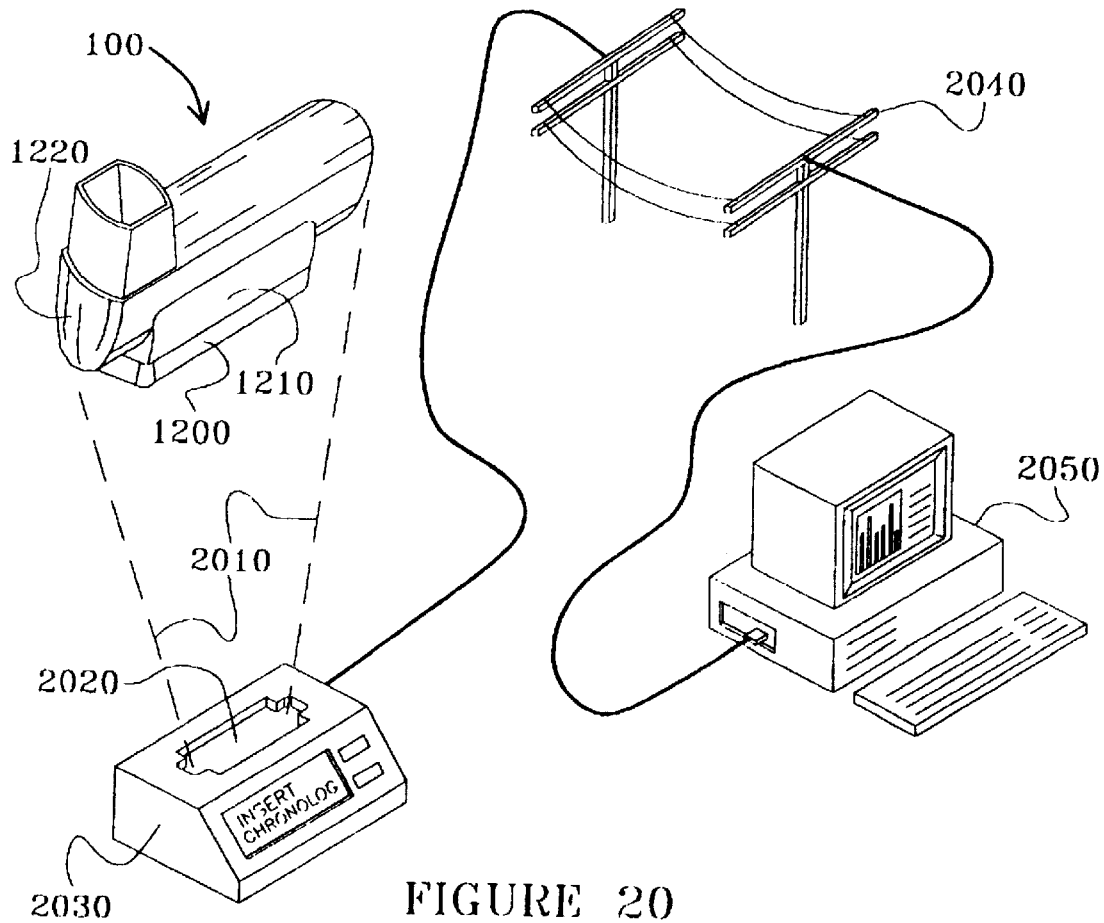

FIG. 12 illustrates an improved accessory style chronolog apparatus along with an adaptable housing of the present invention and a commercially available vial/actuator combination of a typical MDI dispenser;

FIG. 13 is an illustration showing the chronolog apparatus of FIG. 12 mounted via the adaptable housing to the commercially available vial/actuator combination;

FIG. 14 illustrates the details of the control and display panel and the latching mechanism holding the chronolog apparatus to the adaptable housing;

FIGS. 15a and 15b are exploded perspective views revealing the layering of various components comprising the accessory chronolog apparatus in a moisture tight packaging technique and its relationship to the adaptable housing and typical commercially available vial/actuator;

FIG. 16 is a cut away detailed view showing the dynamic sensing arm as it is engaged with the vial/canister and protruding through the housing wall of the commercially available actuator;

FIGS. 17a, 17b and 17c are cross-sectional close-in views of the main three positions of the dynamic sensing arm detailed in FIG. 16 of the present invention with medication vial/canister disengaged, properly seated and fully actuated respectively, within the commercially available actuator;

FIGS. 18a and 18b are detailed side planar illustrations of the accelerometer sensor and reed switch elements which give indications that the medication is properly mixed prior to use as recommended by the drug manufacturer;

FIGS. 19a through 19e are graphic representations of signals generated by the strain gauge dynamic sensing arm and air flow fast response thermistor;

FIG. 20 is an illustration of the improved apparatus 100 along with a docking station of the present invention for temporarily storing data/information and communicating via telephone company lines to a remote personal computer which shall retrieve and analysis the user/patient MDI device performance.

DESCRIPTION OF THE PREFERRED EMBODIMENT

Figure 1:
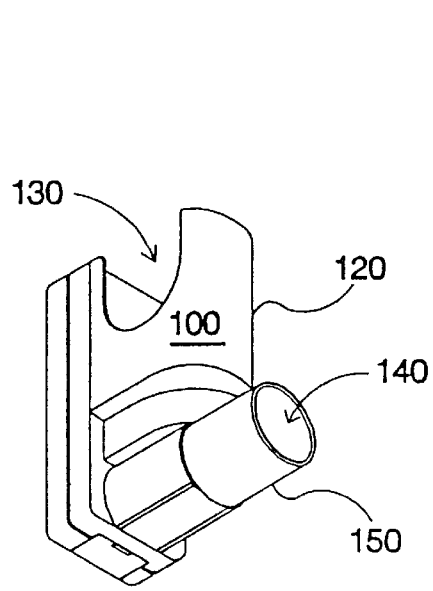
FIG. 1 sets forth a perspective view of present invention.

In FIG. 1 is shown an electronic inhalant device 100 of the present invention suitable for dispensing medicated inhalant in metered dosages. The body housing 120 which is only slightly bigger then and is familiar to a conventional inhalant dispenser having no capability to record events associated with the dispensing of the medication. This miniaturized and familiar feeling body 120 has disposed on the front, a replaceable mouthpiece 150. Conventionally available medicated inhalant canister package would be placed in opening 130 as prescribed by a doctor. The medicated inhalant would pass through opening 140 of mouthpiece when unit is activated.

Figure 2:
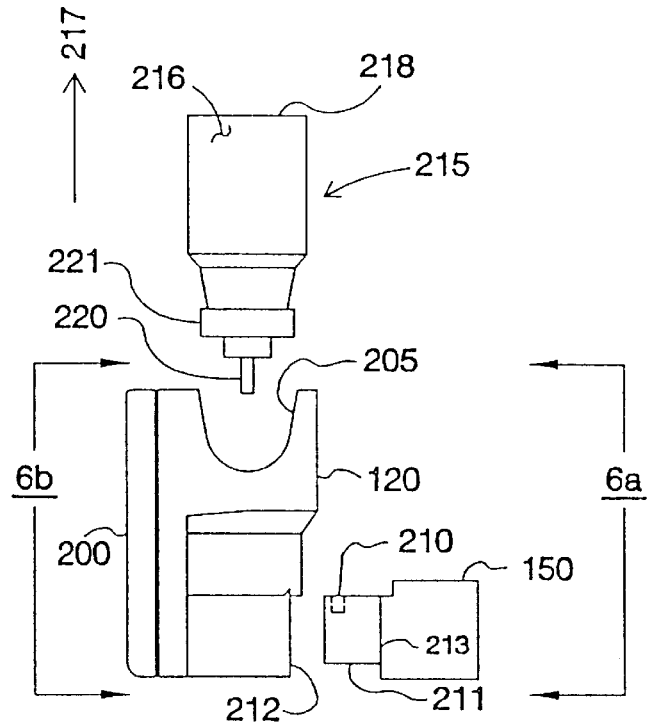
FIG. 2 is a side planar view of the device of the present invention with detachable mouthpiece separated from the main body, and showing a conventional medication inhalant package.

In FIG. 2, the replaceable mouthpiece 150 is shown detached from body housing 120. This feature is to allow for the selection of an appropriate inhalant orifice size or to replace with a new mouthpiece for sanitary reasons. The surface 211 of replaceable mouthpiece 150 mates with receptive opening 212 of the body 120. The mouthpiece 150 would be pushed inward until fully seated at surface 213. Medication inlet 210 is then aligned so as to engage valve stem 220 of the medicated inhalant canister package 215. The medicated inhalant canister package 215 is any of a number of medications conventionally available.

When medicated inhalant canister package 215 is fully seated into body housing 120 so as to engage valve stem 220 with medication inlet 210, finger openings 205 expose the bottom portion 216 of canister 215. By holding canister 215 with thumb and forefinger at canister area 216 through finger opening 205, and pulling in the direction of arrow 217, removes medicant canister from device 100.

Figure 3:
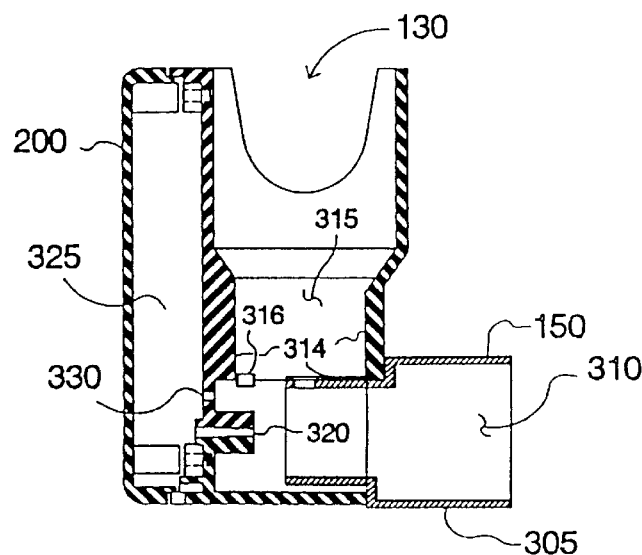
FIG. 3 is a cross-sectional view showing the inner chambers of the present invention.

In FIG. 3, the device 100 is shown in a side cross-sectional view revealing the inner chambers. Chamber 315 is the space which allows the medicated inhalant canister package 215 to be placed. Valve stem 220 and shoulder 221 fit snugly with inner surfaces 314 of chamber 315. There is an air inlet hole 316 which allows ambient air to flow in from opening 130 around sides of canister 215, through the device 100 when medication is being inhaled. This shall be discussed in detail later. Behind electronics access cover 200, is the electronics chamber 325. Orifice 320 allows the main sensing element 425 of FIG. 4 to be substantially in the path of medication flow, and orifice 330 allows the air flow sensing element 435 to be in the ambient air inlet path.

In FIG. 4 shows the electronics assembly 400 comprising electronic circuitry 405, batteries 410, and 411, communication connector 415, main sensing element 425, and air flow sensing element 435 all mounted on a single multi layer printed circuit board 401. The main sensing element 425 is detailed in cross sectional FIG. 4a whereupon a stainless steel support tube 420 is first press fitted to brass ferrule 430 and then affixed to printed circuit board 401 by means of a solder joint 431. The main sensing element 425 in the preferred embodiment is a fast response thermistor manufactured by Betatherm Corp, 910 Turnpike Rd., Shrewbury, Mass. 01545, as part No. 100K6MCA24. The thermistor is affixed to the stainless steel support tube 420 by means of thermally high conductive epoxy adhesive 427 with sensor wires 440 and 441 passing through hollow space 426 of tube 420, brass ferrule 430 and printed circuit board 401. These sensor wire leads are attached electrically to printed circuit board 401 at solder junction 442 and 443. Air flow sensing element thermistor is mounted similarly as sensor 425. It is to be expressly understood that any conventional sensing scheme using, for example a pressure device or an audio element device, could be used instead of the thermistor arrangement disclosed above and that the approach shown in FIGS. 4 and 4a is exemplary of one approach.

In FIG. 5 discloses the present invention illustrated fully assembled. Proximity reed switch sensor 505 indicates to the microprocessor on the electronics assembly 400 that a medicated inhalant canister package 215 is in fact installed into the device 100. As the shoulder 221 of the canister 215 is inserted into position, a magnet 506 is pushed down onto a spring 507 and positioned within the operating field of the proximity reed switch sensor 505. By this means the device 100 knows and logs along with time and date, the number of medicant canisters which were used for any given prescribed period of time. The proximity reed switch sensor, magnet and spring are conventionally available and are commonly manufactured by several sources. The detail of 505, 506 and 507 are not shown in FIG. 5 but shall be disclosed more fully later.

The valve stem 220 which fits snugly into medication inlet 210 of FIG. 2, when activated sprays inhalant medication into the inhalant sensing chamber 510 where sensor 425 of FIG. 4 is substantially in the path. Coincidental to this action, which shall be more fully discussed later, the user inhales causing ambient air to enter through inlet 316 of FIG. 3, monitored by air flow element 435 and proceeds through air passage slots 515. The medicated inhalant propelled spray is ejected through precision orifice, which shall be disclosed in FIG. 6 as 650, and mixes with ambient air in space within dotted lines 520 as it is being expelled out mouthpiece opening 140. This process shall be discussed further in a later section of this disclosure.

Figure 6:
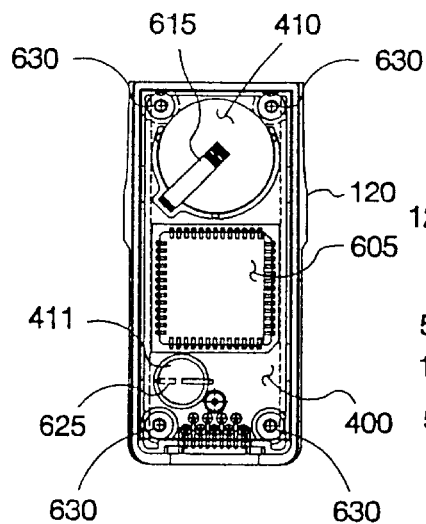
FIG. 6 is a rear planar view of the present invention with access cover removed to reveal battery placement.
Figure 6A:
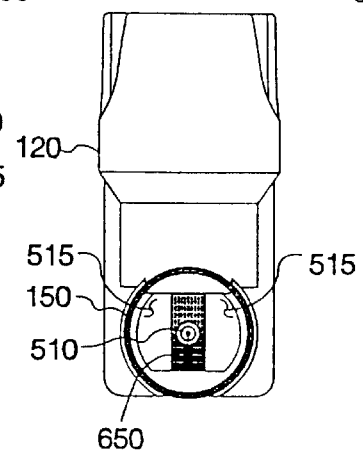
FIG. 6a is a front planar view showing inhalant sensing chamber with precision orifice.
Figure 6B:
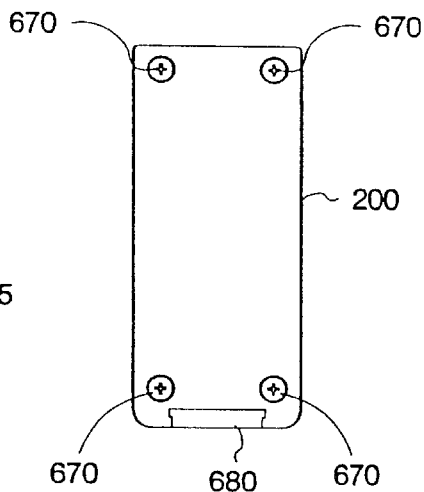
FIG. 6b is a rear planar view of the device of the present invention.

FIG. 6 shows the back side of the device 100 with the electronics access cover 200, as shown in FIG. 6*b*, removed so as to reveal the electronics assembly 400. Threaded holes 630 hold the electronic assembly 400 and electronic access cover 200 in position using machined screws 670 which are receptive to threads in holes 630. A microprocessor 605 is shown on the assembly between the two battery systems 410 and 411. Batteries 410 are the main power to the device and are two conventional 3.0 volt lithium cells. The 3.0 volt battery 411 is to power the ram memory, on other side of printed circuit board not shown, if main batteries 410 are ever removed or become low in energy. Battery 411 provides non-volatility to date and time clock and ram circuitry. It is manufactured by Renata in Switzerland and available through Renata Batteries U.S., Dallas, Tex. 75207, as part number CR927. This power system assures that all logged records are retained in the ram in the event the main power batteries 410 run down and need to be replaced. Battery clips 615 and 625 are provided to hold batteries 410 and 411 respectively in position.

In FIG. 6*a*, the present invention shows within the replaceable mouthpiece 150, the precision orifice 650, inhalant sensing chamber 510 and air passage slots 515. As discussed earlier, the orifice 650 of mouthpiece 150 is selectable by size as needed in various medication types, typically the diameter is 0.022 inches. This is accomplished by replacing the mouthpiece 150 as is appropriate and recommended be medication manufacturers.

Figure 7:
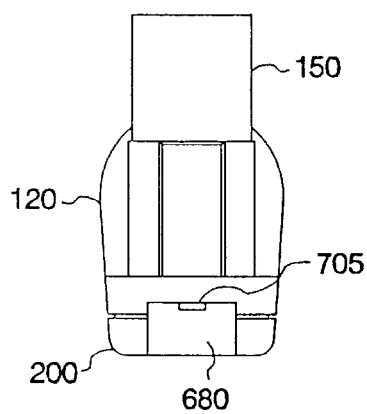
FIG. 7 is a bottom planar view of the device of the present invention.
Figure 7A:
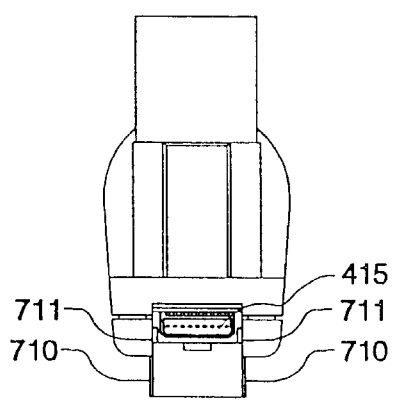
FIG. 7a is a bottom planar view illustrating the sliding communications connector access panel in the open position.

In FIG. 7 shows a communications access panel 680 in the closed position as integrated with body housing 120 and electronics access cover 200. By placing an object, such as a finger nail, in recess 705 and pushing, the panel 680 moves along guide and tracks 710 and 711 respectively as is shown in FIG. 7*a*. Once panel 680 is fully open, the communication connector 415 is exposed and may be connect to for retrieval of captured chronolog data which shall be discussed later.

Figure 8:
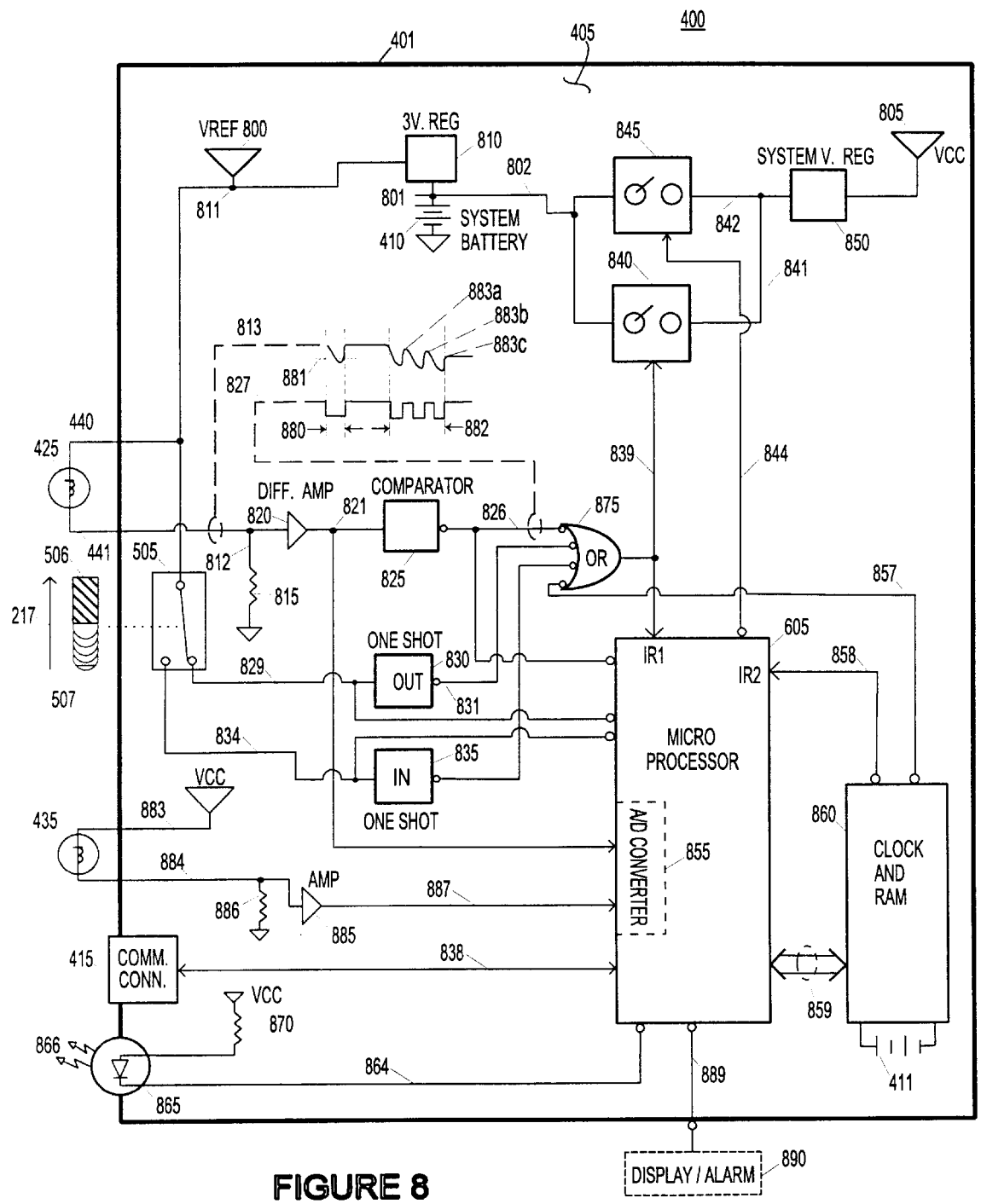
FIG. 8 is a schematic block diagram of the electronics of the present invention.

In FIG. 8 is disclosed a schematic block diagram of the electronic circuitry 405 on printed circuit board 401 of the electronic assembly 400. Main system battery 410 supplies a constant source of power to the input of 3 volt regulator 810 over regular source line 801. Main system battery power is also available to the inputs of electronic switches 840 and 845 over feed line 802. The output of 3 volt regulator 810 provides a constant source of standby power to all essential circuitry (the connections not shown) in addition to what is shown, connections to voltage reference (V Ref) 800 over line 811. The essential circuitry are components which initialize the process of detecting events and shall be discussed in detail later.

The common terminal of proximity reed switch sensor 505 is also connected to V Ref 800 over line 811. Normally closed terminal of reed switch 505 is connected to canister "out" one-shot 830 over line 829 and further connected to microprocessor 605 I/O port. The normally open terminal of reed switch 505 is connected to canister "in" one shot 835 over line 834 and further connected to microprocessor 605 I/O port. The output of the one-shot 830 is connected to OR circuitry 875 input over line 831. Likewise, the output of the one-shot 835 is connected to the OR circuitry 875 input over line 836. The output of OR circuitry 875, over line 839, is connected to control gate of electronic switch 840 and microprocessor 605 interrupt No. 1 (IR1) input. The output of electronic switch 840 is connected to the system voltage regulator 850 over line 841. The system voltage regulator 850 output provides operation power (Vcc) 805 to all circuitry (non standby) which has been shut off to conserve energy. Vcc 805 lines are not shown on the schematic block diagram. Once Vcc 805 has been brought up to power as the proceeding paragraphs shall detail, it is latched-on by instruction of the microprocessor as shall be discussed later in this section. To illustrate the function of the circuitry thus far, when medicated inhalant canister 215 is removed from electronic medicated inhalant chronolog apparatus 100, magnet 506 moves in the direction of arrow 217 by means of spring 507 which releases the alternate action of proximity reed switch 505 to move to its normally closed position. This causes voltage available at input of reed switch 505 to be available on line 829 which functions one-shot 830 so as to provide a momentary pulse to the OR-ing circuitry 875, which in turn activates electronic switch 840 to provide Vcc power to the system for as long as the duration of the momentary pulse generated by one shot 830 (for example 100 milliseconds). Likewise, if a new medicated inhalant canister 215 is inserted into the electronic medicated inhalant chronolog device 100, magnet 506 moves in the opposite direction of arrow 217 compressing spring 507. Magnet 506 effects proximity reed switch 505 to cause available standby power V Ref 800 to be on the normally open terminal providing power over line 834 to function one-shot 835. The momentary pulse output is over line 836 effect OR circuitry 875 and electronic switch 840 similarly to one-shot 830 as described earlier to provide system power Vcc 805. Further description of these functions shall be described later in the section.

Lead 440 of fast response thermistor 425 is also connected to V Ref 800 standby power over line 811. Thermistor 425 is further connected to input of differentiating amplifier 820 on lead 441. The input of differentiating amplifier 820 is also connected to "ground" potential through current limiting resister 815 over line 812. Differentiating amplifier 820 output is commonly connected to comparator 825 and microprocessor 605 analog to digital (A/D) converter 855 input by line 821. The function of amplifier 820 in part, is to "track" the slope of wave form 813. Comparator 825 outputs square wave signal 827 at threshold 881. The threshold 881 shall be discussed in detail later. Signal 827 is presented to the OR circuitry 875 and the microprocessor 605 I/O similarly as other 875 inputs as was described earlier, over common line 826. Again, the OR circuitry 875 functions to power the system Vcc 805 via electronic switch 840 and regulator 850, but in this case for the duration of pulse width 880.

The clock and ram circuit 860 further functions to activate the OR circuitry 875 over line 857. Clock and ram circuitry 860 has its own independent standby power source battery 411. Battery 411 functions to operate the time and date clock at very low levels of energy in addition to maintaining stored data in the ram (random access memory) section of circuitry 860 during periods of main system power Vcc 805 shut-down, as will be fully discussed later. The clock and ram circuit 860 can be pre-programmed to cause a pulse on line 857. This pulse presented to the input of OR circuitry 875 functions to activate electronic switch 840 and system voltage regulator 850 providing power Vcc 805 similarly to functions previously described with one-shots 830 and 835, and comparator 825. All four of these circuits; 830, 835, 825, and 860 serve in part to activate electronic switch momentarily making system battery voltage available to system voltage regulator 850 which in turn activates main system power Vcc 805.

Any time main system power Vcc 805 is activated all associated circuitry which was shut-down to conserve battery energy, comes alive and functions according the rom (read only memory) program stored within microprocessor 605. Upon initialization of microprocessor 605, program instructions command electronic switch 845 to activate over line 844. System battery is now also provided to system voltage regulator 850 over line 842. The purpose of electronic switch 845 is to "latch ON" main system power Vcc 805 to all appropriate circuitry to function programmed instructions beyond the momentary pulsing activation interval generated at the output of OR circuitry 875 as was earlier described.

The air sensing element thermistor 435 functions similar to the main sensor 425 except it is powered via Vcc 805 over line 833. Thermistor 435 is connected directly to A/D converter 855 through amplifier 885 over lines 884 and 887, with current limiting resistor 886 providing path to ground. During powering-up, the fast response thermistor element 435 self heats and when the ambient air passes through air inlet 316, would cause a drop in temperature. If no air is being drawn through ambient air inlet 316, the rate of temperature would continue to rise. The A/D converter 855 monitors these characteristics determining proper inhalation.

Microprocessor 605 once initialized, responds to signals presented at its interrupt inputs IR1 and IR2. IR1 signal over common line 839 is indicative of activity generated by main sensing element 425 and proximity reed switch 505, the microprocessor 605 will scan I/O port to see which one of lines 829, 834, or 826 has toggled and shall proceed to predetermined programmed instructions based on which line is active. Additionally, when signal is present on line 826, microprocessor 605 activates function of its internal A/D converter 855 to be responsive to any signal present over line 821 and on line 887. The result of signals, and there characteristics, of 826, 821, 880, 881 and 882 are due to the activation of dispensing medicated inhalant and shall be more detailed later under the operations section of the present invention. The IR2 interrupt input of microprocessor 605 responds to activation generated from the clock function of clock and ram circuit 860 over line 858. This interrupt is indicative of some predetermined programmed instruction, for example, "alarm" to take medication. Line 889 delivers informational data, instructions and alarm signals from microprocessor 605 to device 890 (which shall be further discussed in FIG. 11 herein). Data and address lines 859 are conventionally connected between microprocessor 605 and clock and ram circuit 860, and functions as necessary according to conventional programming technique. Valid event LED (light emitting diode) indicator 865 illuminates when microprocessor 605 toggles output line 864. Current limiting resistor 870 functions to complete LED indicator 865 circuit. Illumination 866 serves as feedback to the user of the electronic inhalant device 100 when optional display/alarm device 890 is not present. It is understood that a tone generator could be substituted for an audible effect instead of the visual effect of the LED 865 circuit. Finally communications connector 415 is connected to the microprocessor 605 over bi-directional transmit/receive line 838. Connector 415 also provides external system power directly to system regulator 850 (not shown) when an external communications cable is connected to the electronic inhalant device 100 conserving battery life. This feature shall be further discussed in FIG. 10. All components illustrated in schematical block diagram in FIG. 8 are representative of functional components and are commonly available in a diversity of configurations by many manufacturers. Such components are easily connected to one another by anyone skilled in the art as set forth in the diagram of FIG. 8. It is to be expressly noted that while individual sensor elements have been set forth and discussed for electronics shown in FIG. 8, in the preferred embodiment, other sensor elements may be substituted to result in the same function. For example, thermistor sensors 425 and 435 which detects change in temperature as medicated inhalant passes in the approximate path creating wave form 813 could be produced by audio elements (and appropriate associated circuitry) detecting change of sound as medicated inhalant passes in the approximate path of sensor elements 425 and 435. The signature of the sound, both sonic and ultrasonic, created as the inhalant spray being, first passing through the inhalant sensing chamber 510 and, second expelling out of precision orifice 650 expanding and mixing with ambient air in the chamber 310 would have exact and repeatable characteristics. Or one further example, pressure or piezo sensors detecting changes in pressure as medicated inhalant passes in the approximate path of sensor elements 425 and 435. These and other sensor element schemes all could be made to produce similar wave forms 813 and 827 and A/D signals present on lines 821 and 887, to provide input signals of the present invention.

Figure 9:
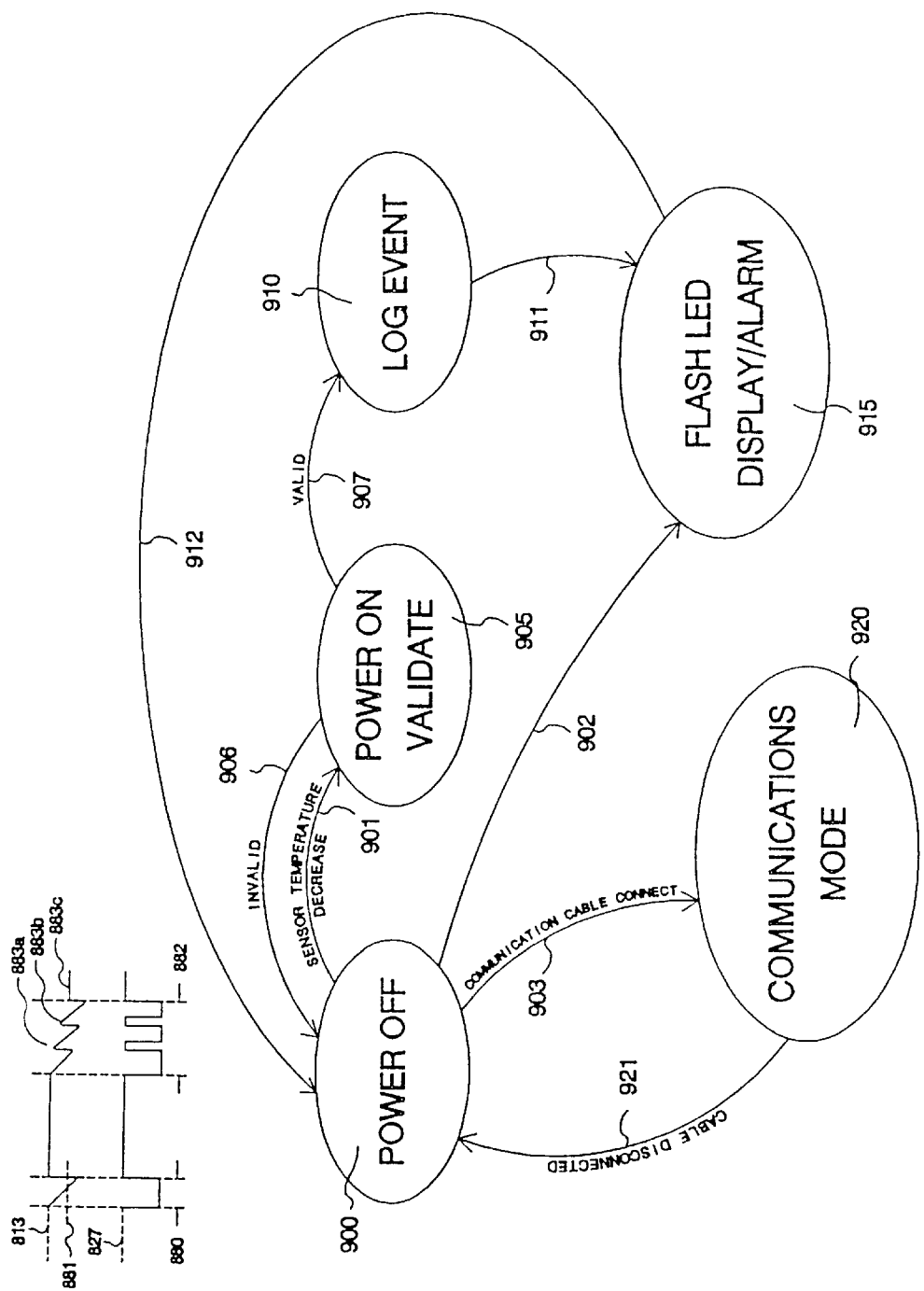
FIG. 9 sets forth a state table for the control circuit of FIG. 8.

In FIG. 9, is set forth the flow of logic in the form of a state table concerning the sensing elements for the operation of the electronic circuitry 405. This process is driven according to instruction program code conventionally written as executions recommended by components manufacturer data sheet recommendations for any desired result as may be capable of the component, and anyone skilled in the art could write such code. In FIG. 9, the following occurs. Power off state 900 normally exists in a standby mode. In the event an activity is sensed, such as a detected rate of temperature decrease of sensor 425, the power off state 900 enters the power on validate state 905 over path 901. It is in this state, that the electronic switch 840 activates system voltage regulation 850 to provide momentary Vcc 805 power to system to determine the validity of the activation. If the result of signals 826, 821, 880, and 881 (and their characteristics) meet the criteria wave forms 813 and 827 of FIG. 8, indicating an activation of dispensing medicated inhalant, the log event state 910 is entered as valid over path 907. The event would be logged in memory complete with date and time, and magnitude of signal present on line 821 indicating the strength of dosage being dispensed and magnitude of signal present on line 887 indication the air flow through ambient air inlet 316. If criteria wave form 813 and 827 are not the expectant shape and minimum threshold level 881, the system enters back to power off state 900 over path 906 and shut-down to a standby operation once again.

It is important to understand that "validate signals" is part of the management of state 905 and as such determines if the activation of the device 100 expelling medicated inhalant is properly dispensed in user's mouth and respiratory system and respiratory system, or otherwise expelled into surrounding ambient air.

From the log event state 910 the system enters into the flash LED/display/alarm state 915 over path 911 to provide feedback of the event to the user before entering back to the power off state 900 for standby shut-down over path 912. The flash LED/display/alarm state 915 may be entered directly from the standby 900 mode over path 902, as is in the case of clock and ram circuit 860 of FIG. 8, would initialize upon a predetermined programmed schedule to remind user to take medication.

It should be explicitly understood, that state 915 is symbolized as a general system configuration. It may be as simple as the LED indicator 865 or more complex as display 890 (which shall be elaborated in second embodiment of FIG. 11 in detail), or may not exist at all. In the later case, path 912 would come directly from state 910 upon completion of logging event to return to standby power off 900. This later case is a zero feedback configuration which is desirable in "blind" testing patients to serve as medication dispensing behavior analysis.

Importantly, the teachings of the present invention provides feedback to the user as may be necessary. For example, device 100 having installed a placebo canister 215, is useful for helping new patients to get use to the timing in activation of the device and inhaling. The flash LED/display/alarm and sensor capability would indicate such feedback as; improper synchronization of inhaling and inhalant release, inhaling too slow or too fast, and inhaling too hard or too soft. All events are monitored and logged. Once the new patient was comfortable with proper operations of self administering the inhalant, they could use a less complex display 890 configuration of the device 100.

To illustrate further the sensing elements and associated circuitry, the power on state 905 would be entered from standby power 900 over path 901 for each of the events indicated in time reference 882. Time 882 is a possible wave form indicating 3 valid recursive actuations of the electronic inhalant device 100. Note that each recovery peak 883*a*, 883*b* and 883*c* become less and less from the original starting temperature as is indicated at the start of time at wave form 882 of signal 813. By means of differentiating amplifier 820 in FIG. 8, the threshold 881 is proportionally to each descending starting point of recursive activations 883*b* and 883*c* respectively. Wave form 827 of time 882 indicates that proper threshold criteria has been meet for each activation and would have entered power on validate state 905. This together with signals present on lines 821 and 887 as interpreted by A/D converted 855 would constitute a valid magnitude of signal indicating a proper dosage (or less than proper dosage as the case may be), whether or not inhalant was properly expelled into user's mouth, and log event in state 910. If less then full dosage is discerned, which would be indicated in the feedback flash LED/display/alarm state 915 (as may be possible when medicated inhalant canister package 215 is empty or near empty), would prompt user to actuate device 100 a second, or in the case of the above illustration a third time. For each of the three activations in the above illustrated example, the full cycle from powering up, validating signals, logging events, and as may be appropriate flashing LED or displaying or alarming, to power shut-down to standby would occur between each recursive activation because of the speed and efficiency of electronics assembly 400.

Similarly, when system activation is due to activity responsive to proximity reed switch sensor 505 (not shown in FIG. 9), the power on validate state 905 would be entered and further enter state 910 to log event and give feedback of event in state 915.

When communication connector 415 has been connected to external data retrieval device (disclosed in FIG. 10), system enters into communication mode state 920 over path 903 and system becomes responsive to the external commands. The down-loading of possible entries would be; interval schedule of medication for auto alarm indication, quantity of dosage, type of medication, and patient's name. The up-loading function would extract all chronologically stored data including an instrument diagnostic report listing sensor behavior and battery supply voltage levels. These features shall be discussed further in the disclosure of the present invention in FIGS. 10, 11 and operation. The powering of system regulator 850 of FIG. 8 is supplied directly from external source via connection to communication connector 415. Once disconnection from communication connector 415 happens, the communications mode state returns back to the power off state 900 and shuts-down to standby.

Figure 10:
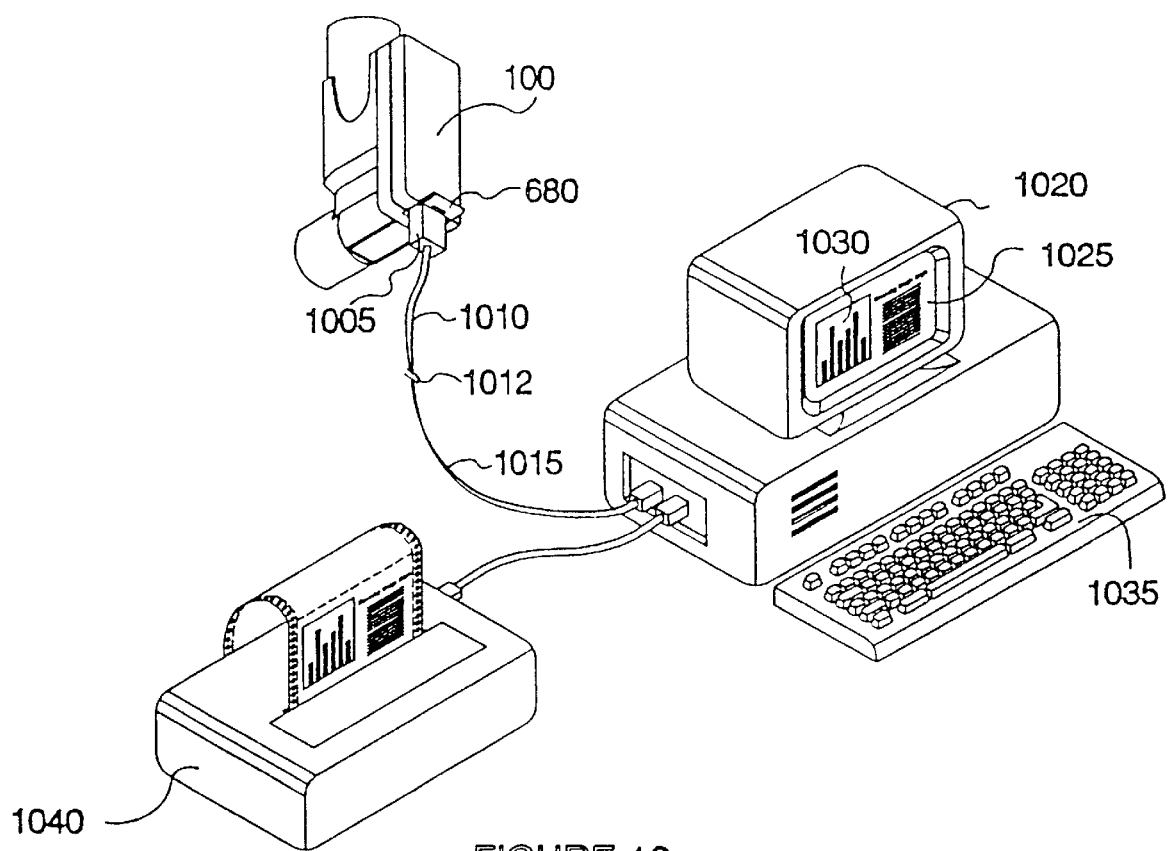
FIG. 10 sets forth an illustration of the system of the present invention being connected to a data retrieval device.

In FIG. 10 the electronic inhalant device 100 has its communications access panel 680 in the open position and communications cable connector 1005 connected to matted receptacle 415 mounted on the electronics assembly 400 as identified in FIG. 4. Communications cable 1010 and 1015 attach to computer 1020. The junction 1012 illustrates that communication modems may be in the data path transmission over cables 1010 and 1015 for remote retrieval of chronolog stored records. Computer 1020 accesses the data base in the chronolog device 100 for retrieval and analysis of the medication administered and is displayed in tabulated statistical form 1025 and graphically as in 1030. Such information may be stored in computer memory for combining with other similar chronolog users data and further printed to hard copy utilizing printer 1040. Keyboard 1035 is manipulated in conventional manner to program device 100 for scheduling if required by doctor. Retrieved information 1025 and 1030 also could represent a diagnostic report of the device 100 over the full recorded period of time which includes battery and sensor response. This information, under analysis, indicates if the instrument was functioning properly. The computer, printer, cabling and connectors are all conventional and well known and are easily operable by anyone skilled in data handling.

The emphasis here is that positive reporting of prescribed medication is diligently recorded and analyzed to assure the benefits of the medicine doing what the doctor prescribes based on reliable feedback information.

Figure 11:
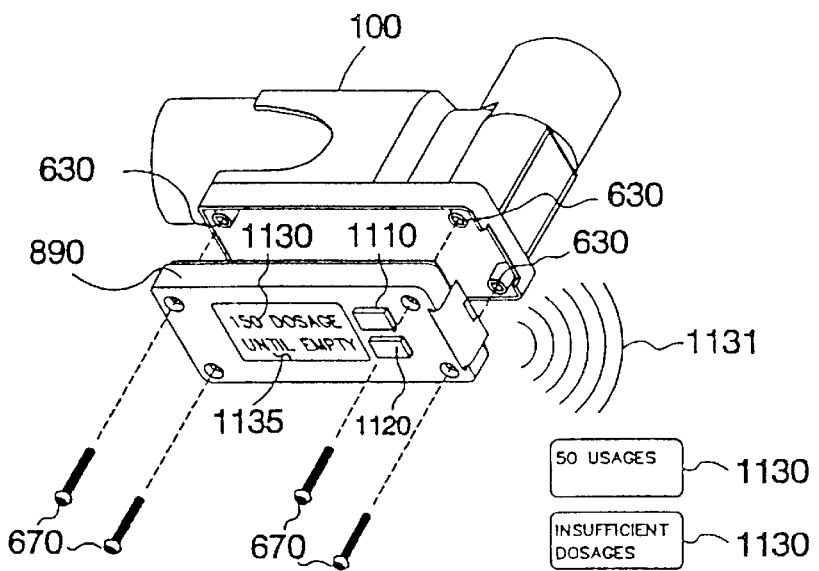
FIG. 11 sets forth a rear exploded perspective illustration of a second embodiment showing an information display of the device of the present invention.

In FIG. 11 is shown a second embodiment of the present invention where display/alarm module 890 replaces the rear electronic access cover 200. This miniaturized module 890 attached to device 100 as was similarly disclosed in FIG. 6*b* utilizing screws 670 and threaded holes 630.

The LCD (liquid crystal display) 1135 and push-bottoms 1110 and 1120 are interconnected to microprocessor 605

(connections not shown) conventionally and respond to diverse program routines. One example of such routine is when the user would depress menu selection push-button 1110 until desired option appears in the display 1135, for example (NUMBER OF DOSAGES REMAINING). The user would then depress activate request push button 1120 for the response to the request, for example (150 DOSAGES UNTIL EMPTY) message 1130. The device 100 could know this information if it were programmed with the typical number of metered dosages as is purported by the medication manufacturer. Else the display would simply indicate, for example, (50 DOSAGES USED THIS CANISTER) as a message 1130.

It is expressly understood that the type and meaning of messages 1130 and alarms 1131 indicated and displayed by module 890 is as varied as medications and concerns that doctors may have, and that the present invention contemplates, and is suited to deliver fully, utilization to satisfy the need.

In operation, the present invention device 100, being miniaturized, portable and having a familiar body housing 120 to users as non electronic medication inhaler dispensers, the user would install a conventional medication canister 215 in opening 130 for the dispensing of medication. Proximity reed switch 505 senses the canister being present in system and event is logged in non-volatile memory 860.

As user desires a dose of medication, device 100 (which fits easily in palm of hand) is placed in front of user's face as FIG. 1 shows in orientation, with mouthpiece 150 positioned such within that user's lips are around surface 305 so as to have opening 140 directly accessible to user's inner mouth and throat. The user would place forefinger of hand holding the device 100 in area 218 of the canister and press conventionally downward, (approximately ⅛ inch) to release one metered dose of medication from canister 215. Valve stem 220 actuates the release as is seated snugly in medication inlet 210. Fast response temperature thermistor 425, being substantially in the path of inhalant flow within sensing chamber 510, experiences a rapid drop of temperature with respect to quiescent temperature just previous to actuation of valve 220. The physical time of actuation inhalant release is typically 200 milliseconds. At the leading edge of the previous process, the microprocessor 605 has been initialized and latched operation power via electronic switch 845. Validation of signals generated by differentiating amplifier 820 and comparator 825 is processed together with 855 A/D converter signals to determine the positive medication inhalant release, and its strength with respect to magnitude and duration. Air flow thermistor 435 monitors the ambient air inlet 316 which allows air flow into the area of the inhalant sensing chamber 510 caused by the user's inhalation. The released medication and ambient air mix expands within chamber 310 area indicated by dotted lines 520 and is expelled out of mouthpiece opening 140.

An important feature of the present invention is expressly understood that the user is identified as positively inhaling the medication by the device 100 as prescribed (as opposed to simple being dispensed). This is defined as the medication being administered into the user's mouth, throat and respiratory system as intended. For example, actuation of the device 100 to test the function of the medication canister 215 without having mouthpiece within user's lips, would expel the medication into surrounding atmosphere. The fast response sensors 425 and 435 would produce different wave form characteristics than those disclosed in referenced time 880 and on A/D signals of lines 821 and 887 of FIG. 8. This is possible by the distinct signature developed by the user drawing ambient air through inlet 316 and inhalant expanding within area 520 before being expelled. Thus, if accidental actuation, or misuse of device 100 occurs, appropriate event recording is chronologged and further complete positive analysis is possible by the prescribing doctor.

DESCRIPTION OF FIGS. 12 THROUGH 20

FIGS. 12 through 20 show an alternative embodiment of the present invention incorporating a number of refinements and improvements to the embodiment shown in FIGS. 1 through 7. The apparatus 100 has been reduced to an accessory module mounted onto a commercially available vial/actuator combination. This accessory module allows the existing Food and Drug Administration (FDA) authorized and approved device combinations to be monitored without re-approval.

FIG. 12 illustrates the first improvement, an accessory style chronolog apparatus 1200 along with an adaptable housing 1210 of the present invention. A commercially available vial/actuator combination 1220 is of a typical metered dose inhalant (MDI) dispenser. The adaptable housing 1210 has a mating structure 1230 and 1240. The mating structure 1230 is formed to mate with the accessory chronolog apparatus 1200 and is consistent to all such adaptable housing 1210. The mating structure 1240 is formed to mate with each individual configured design of the commercially available vial/actuator 1220 combination MDI dispenser. Currently there are approximately twelve pharmaceutical manufactured commercially available vial/actuator 1200 combinations of MDI dispensers, each having its own unique package design. The adaptable housing 1210 is intended to economically facilitate the attachment (piggyback style) of the accessory chronolog apparatus 1200 to each of the uniquely designed commercially available vial/actuator 1220 combinations of MDI dispensers.

The adaptable housing 1210 has a hole 1250, and the commercially available vial/actuator 1220 has an access hole 1260 which has been cut into the wall during the installation. The access holes 1250 and 1260 shall be more fully disclosed later.

FIG. 13 is an illustration showing the chronolog apparatus 1200 of FIG. 12 mounted via the adaptable housing 1210 to a typical commercially available vial/actuator combination 1220. Collectively, these improved features comprise the alternative embodiment of the improved apparatus 100 of the present invention. The features significantly broaden the application and functionality of the apparatus 100 without changing the familiar physical package and feel of the originally designed commercially available vial/actuator 1220 combinations of MDI dispensers which were test and FDA authorized and approved.

In the embodiment shown in FIGS. 1–7 and 11, the medication vial or canister is inserted into a dedicated actuator constructed into the chronolog housing, and therefore is not tested and FDA authorized as is the pharmaceutical manufacturer's actuator. This is typical to all prior art. Although these prior art systems may be suitable for some applications, it is obvious the improved accessory chronolog 1200, mounted to tested and FDA authorized commercially available vial/actuator 1220 combinations of MDI dispensers via a suitable adapter housing 1210 is a substantial improvement thereof. This improved accessory chronolog 1200 requires no extraordinary risk as to possibly altering, or interfering with, the medication delivery.

In FIG. 14 is shown the details of a control and display front panel 1410 of the accessory chronolog 1200. The panel 1410 has a display window area 1420 and a control entry push-button area 1430. Another improvement arises in FIG. 14, showing an alternative embodiment having on the front of the panel 1410 an air holes inlet 1440 and wireless data communications infrared (IR), transmitter 1450 and receiver 1460. These elements, shall be discussed further in later sections of this disclosure.

The accessory chronolog 1200 is attached to the adaptable housing 1210 via a snap latch system 1470. There are two each snap latches 1470 on both sides of the housing 1410 to securely hold the assembly between the devices 1200 and 1210. The plastic molded housings of the devices are conventionally produced with said snap latches incorporated therein. A special tool, conventionally available for such purposes, allows the two structures 1200 and 1210 to be separated for service or maintenance. The adaptable housing 1210 is affixed permanently to the commercially available actuator 1220 dispenser as shall be detailed in FIG. 15.

FIGS. 15a and 15b are exploded perspective views revealing the layering of various components comprising the accessory chronolog apparatus 1200 in a moisture-tight packaging technique, and its relationship to the adaptable housing 1210 and typical commercially available vial/actuator 1220. The two views of FIGS. 15a and 15b clearly show the detail in its assembly and the economy of space in its design.

A housing 1510, has affixed to its top side a sub-PCB (printed circuit board) assembly 1515. The sub-PCB has on its underside a piezo audio transducer 1520 and on the top side a "dome" push-button 1525 switch circuit. The front panel 1410 is processed with nomenclature, product name, etc. in colored inks (leaving a clear window area 1420 of FIG. 14) and laminated over the sub-PCB 1515 onto the top side of housing 1510. The underside of housing 1510 has space provided for a battery 1530, an LCD display 1535 and a main-PCB assembly 1540. In the preferred embodiment, a gasket 1545 is fitted around the inner edges of the housing 1510 underside and covered with an appropriate plastic cover (not shown so the details of the components may be more easily displayed). Note that the housing 1510 has molded reliefs allowing the above listed components, 1515, 1520, 1525, 1410, 1530, 1535, 1540 and 1545 to smoothly fit into a composite, moisture-tight assembly comprising the accessory chronolog apparatus 1200. It should be understood that, alternatively, a "potting" compound may equally achieve a moisture tight barrier instead of the gasket 1545 and plastic cover.

On the main-PCB, are attach a reed switch 1550 and a strain gauge with dynamic sensing arm 1555. The reed switch 1550 is under the protective moisture barrier, but the dynamic sensing arm protrudes outwardly through the moisture barrier and is aligned adjacent to the hole 1250 in the adaptable housing 1210. The reed switch 1550 is adjacent to an accelerometer sensor 1565 affixed in a cavity 1566 of the adaptable housing 1210. A fast response thermistor 1560 is mounted on the main-PCB 1540 over a small air hole passage located on the edge of the main-PCB behind the dynamic sensing arm 1555. Note that the alignment of the fast response thermistor 1560 is over an air channel 1561 built into the housing 1510. A more detailed description of the sensing components: reed switch 1550, strain gauge with dynamic sensing arm 1555, air flow fast response thermistor 1560 and accelerometer 1565 functions, shall be disclosed latter.

FIGS. 15a and 15b further show the mounting arrangement of the adaptable housing 1210 to a commercial actuator 1575 of the vial/actuator combination 1220. As was previously stated, the adaptable housing 1210 is custom made for each commercial vial/actuator combination 1220 manufactured design and is intended to be affixed on the opposite side from a mouthpiece 1585. A "mounting jig" (not shown) simply locates the position of the small access hole 1260 in mounting area 1580 so the hole can be "punched" in the wall of commercial actuator 1575 with proper alignment. The adaptable housing 1210 has "high tac" adhesive applied to its surface 1570 and mounted such that hole 1250 of adaptable housing 1210 is aligned over the punched access hole 1260 in mounting area 1580 of commercial actuator 1575. The adaptable housing is permanently bonded to commercial actuator 1575 via the adhesive in this manner. A conventional medication vial/canister 1590 is shown separated from the commercial actuator 1575 in FIGS. 15a and 15b.

In FIG. 16 is shown a cutaway detailing a view of the strain gauge dynamic sensing arm 1555 as it is engaged with the vial/canister 1590 and protruding through the hole 1260 of the housing wall of the commercially available actuator 1575. Note that the adaptable housing 1210 is not shown in FIG. 16 to provide a better illustration. Further, the accessory chronolog apparatus 1200 is shown with its moisture barrier removed so that the sensing elements are revealed on the main-PCB 1540.

The strain guage dynamic sensing arm 1555 is comprised of three sections: a solder pad 1610, a strain gauge sensing area 1620 and a contactor 1630. The dynamic sensing arm is made of beryllium copper and has a narrowing in shape at the strain gauge 1620 mid section which allows a focus of flexibility. The top contactor 1630 section is made wider and is folded to create more rigidity at the top. The solder pad 1610 section is firmly attached by means of solder, to the main-PCB 1540. The tip of the top contactor 1630 section makes physical contact to a surface 1640 of the vial/canister 1590 within the commercial actuator 1575.

FIG. 16 also shows the air flow, "very small" fast response thermistor 1560, mounted over a hole at the edge of the main-PCB 1540 and the location of the reed switch 1550. Again, the location and the relationships of these sensors shall be discussed further in a latter section of this disclosure.

FIGS. 17a, 17b and 17c are cross-sectional close-in views of the main three positions of the dynamic sensing arm 1555 detailed in FIG. 16 of the present invention. The medication vial/canister 1590 is shown in FIG. 17a as being disengaged, as it would be if the canister was being removed or reinstalled during a replacement with a new vial/canister 1590. The canister has a stem 1710 which is received into an aerosol chamber structure 1720 during an installation. FIG. 17c shows typical delivery pattern 1730 of medication as it is being dispensed through the mouthpiece 1585 of the commercial actuator 1575.

It is important to understand that the design and detail of the stem 1710, aerosol chamber structure 1720, delivery pattern 1730, mouthpiece 1585, actuator 1575 and vial/canister 1590, all comprising the commercially available vial/actuator combination 1220, are the proprietary interest of the pharmaceutical manufacturer. Importantly, these elements were the subject of the tens of million of dollars of testing by each of the pharmaceutical manufacturers in the FDA approval and authorization of their drugs. The accessory chronolog 1200, when mounted to the commercially availably vial/actuator combination 1220, become a means to effectively monitor the compliance of the medication drug to the physician's prescribed regimen, without any interference or alteration to the delivery of said medication drug as was tested by its manufacturer.

The strain gauge dynamic sensing arm 1555 is shown in FIG. 17*a*, as would be consistent with the vial/canister 1590 disengaged or removed from actuator 1575. Note the strain guage sensing area 1620 of the dynamic sensing arm 1555 is "relaxed", having no tension forced upon it. In FIG. 17*b*, showing the vial/canister 1590 properly seated with stem 1710 engaged in aerosol chamber structure 1720, the tip of the contactor section 1630 makes contact with the surface 1640 of the vial/canister 1590. The strain guage sensing area 1620 of the dynamic sensing arm 1555 now has tension forced upon it. As the vial/canister 1590 is "squeezed" (the act of pushing the vial/canister 1590 down into the actuator 1575 causing a metered dose of medication inhalant to be released through the aerosol chamber structure 1720 and dispensed as pattern 1730 out mouthpiece 1585), as indicated in FIG. 17*c*, the dynamic sensing arm 1555 shows the strain guage sensing area 1620 as having greater tension forced upon it.

FIG. 17*c* also shows the air flow path starting from the air holes inlet 1440, through the air channel 1561 and through the main-PCB 1540 at the edge where the air flow sensor fast response thermistor 1560 is mounted. The air flow continues through the access hole 1260 in the wall of the actuator 1575 that the dynamic sensing arm 1555 is also extended through. It is important to understand that when the user is inhaling the medication by breathing in, ambient air would enter normally into the actuator 1575 around the sides of the vial/canister 1590, as is intended by the pharmaceutical manufacturer. Only a small fraction of ambient air enters through the accessory chronolog apparatus 1200, which allows the sensing of air flow. This channel of a fraction of the ambient air which enters the actuator 1575, has no interfering or altering effect of the medication being delivered out the mouthpiece 1585 of the commercially available vial/actuator combination 1220. The "states" of the air flow, as sensed by the fast response thermistor 1560 and the various tensions of force as they are applied to the strain gauge sensing area 1620 of the dynamic sensing arm 1555, shall be further discussed latter.

FIG. 18*a* and 18*b* are detailed side planar illustrations of the accelerometer sensor 1565 and reed switch 1550. The simplified accelerometer 1565 is comprised of a small plastic tube 1810, a cylindrical magnet 1820 and a compression spring 1830. The magnet 1820, having a magnetic field 1840, causes the reed switch 1550 to actuate (or close) when the magnetic field comes within proximity. The compression spring 1830 holds the magnet 1820 out of the range that the magnetic field 1840 can not affect the operation of the reed switch 1550 during quiescent states: the quiescent state being any of normal portability of the apparatus 100 to include being carried in a purse, pocket, etc., or subject to any motion normal to a user's mobility. A deliberate action, consistent with the instructions by the pharmaceutical manufacturer in the agitation or mixing of the medication within the vial/canister 1590, is sensed by the accelerometer. The "inertia-force", indicated by arrows 1850, causes the collapse of the compression spring 1830 as the mass of the magnet 1820 pushes against it so as to position the magnet 1820 and its magnetic field 1840 to effect the activation of reed switch 1550. It is expressly understood, that the amount of inertia-force to collapse the compression spring 1820, which allows the reed switch to activate by means of the magnet, is selected to directly correlate with the proper amount of pre-mixing of the medication as recommended by its manufacturer. The advantage of the alternative embodiment of the improved invention is, with respect to this determination of proper pre-mixing as opposed to a simple indeterminate "shaking", which may result in un-mixed (concentrated or diluted strengths) medication being dispensed.

Figure 19A:
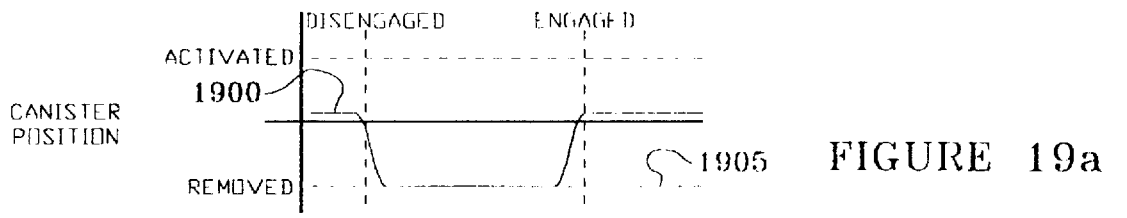

In FIGS. 19*a* through 19*e* are shown graphic representations of signals generated by the strain guage dynamic sensing arm 1555 and air flow fast response thermistor 1560. FIG. 19*a* shows the electrical signal generated by the strain guage dynamic sensing arm 1555 as the vial/canister 1590 (as shown in FIG. 17*a*) is being disengaged (removed) and then engaged (re-installed). Note that wave form 1900 has a stable quiescent state at the beginning of the curve, as would be consistent with FIG. 17*b* showing the apparatus 100 ready for use in a normal standby state. As the wave form progresses in FIG. 19*a*, the vial/canister is detected as being removed as the curve falls to the dotted line 1905. Wave form 1900 shows the signal generated back to the normal standby state as detection indicated that a vial/canister is re-installed. The transitions between the normal standby state and vial/canister being removed or re-installed are dynamic, indicating that the vial/canister is fully seated into aerosol chamber 1720 as shown in FIG. 17*b* or just engaged but not fully seated. Audible and/or visual feedback could be indicated by means of the piezo transducer 1520 or LCD display 1535 to the user, indicating such miss installation of the vial/canister 1590, and could prevent an improper attempt by the user to dispense medication.

Figure 19B:
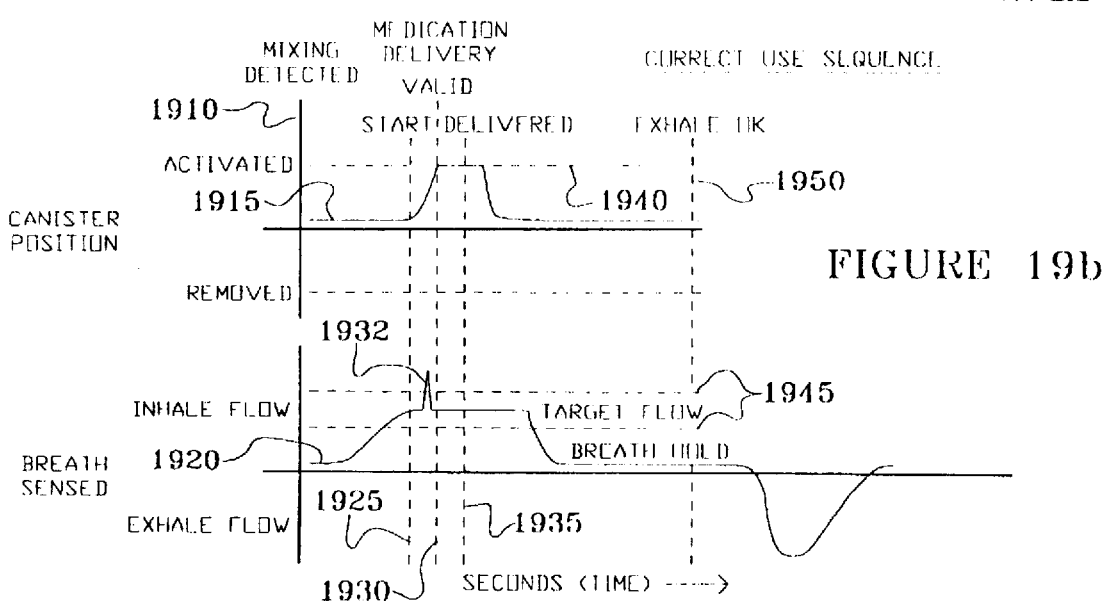

FIG. 19*b* shows a correct use sequence of proper activation of the vial/canister 1590 shown as wave form 1915 and the user/patient's breathing technique as shown as wave form 1920. The sequence starts as a mixing detected 1910 activates by the system as the accelerometer and reed switch meets proper mixing criteria (as recommended by the pharmaceutical manufacturer). The strain gauge dynamic sensing arm and air flow fast response thermistor sensors are powered-up and would be indicated as the beginning of wave forms 1915 and 1920 respectively. The user/patient would begin to inhale, striving for a proper inhalation rate, and then he or she would "squeeze" the vial/canister 1590 into the commercial actuator 1575. The wave form 1920 shows that the user achieved a target flow 1945 rate prior to squeezing the vial/canister. When the medication is discharged out of the valve stem 1710, the instantaneous pressure change creates a perturbation in the ambient air which is passing through the air hole inlets 1440. The result of this momentary perturbation of air flow causes the fast response thermistor 1560 to "peak", producing a medication discharge signal 1932. After the medication has been fully released from the vial/canister, the perturbance in air flow ceases and the medication discharge signal 1932 reverts back to the patient's inhalation signal that is then being sensed as wave form 1920 continues. Wave form 1915 shows that a actuation 1940 was achieved when the vial/canister started 1925 the squeezing process and that it was fully squeezed (depressed into the actuator 1575) indicating a valid 1930 state, the vial/canister would be consistent with FIG. 17*c*. Wave form 1915 further shows that the vial/canister was released (from it being squeezed) well after the typical time medication of a metered dose has been delivered, indicated by dotted line 1935. It is import to understand that a valid delivery of medication signal is produced only if the valid state 1930 and the medication discharge signal 1932 are achieved. In this manner, the signal reliably indicated that the valve stem 1710 was fully compressed and a full measure of medication was positively released for inhalation. Also, wave form 1920 further shows the user continued to inhale well after the medication was delivered and, finally, the user held their breath beyond the exhale OK 1950 dotted line before exhaling (as indicated on wave form 1920). Note, the negative portion of the curve in wave form 1920, indicated beyond the exhale OK 1950 dotted line, is created by the user/patient exhaling into the apparatus 100 (at least for a fraction of a second). This would be necessary so that a "time stamp" could be registered to the event of exhaling only after a proper period of time in holding breath.

It is of significant importance that each MDI usage be properly executed to achieve the medication's intended result. The above correct use sequence of FIG. 19b, can be enhanced by the apparatus 100 as, for example, audible tones emitting feedback of the use in the sequencing of the maneuver. That is: when an idle target flow 1945 inhalation rate is achieved, when the user should squeeze at (start 1925) and when a fully and valid 1930 activation 1940 was achieved, when to stop inhaling and hold breath, and, finally, when to exhale at exhale OK 1950 time. Such sequencing of tones would be especially valuable for user/patient's just learning to use an MDI device as a training instrument. Of course, its value to ensure compliance during drug trials would prove to be of importance being that each indicated event is chronologically recorded in proper sequencing, indicating that the medication was properly delivered and properly received into the respiratory system of the user/patient.

Figure 19C:
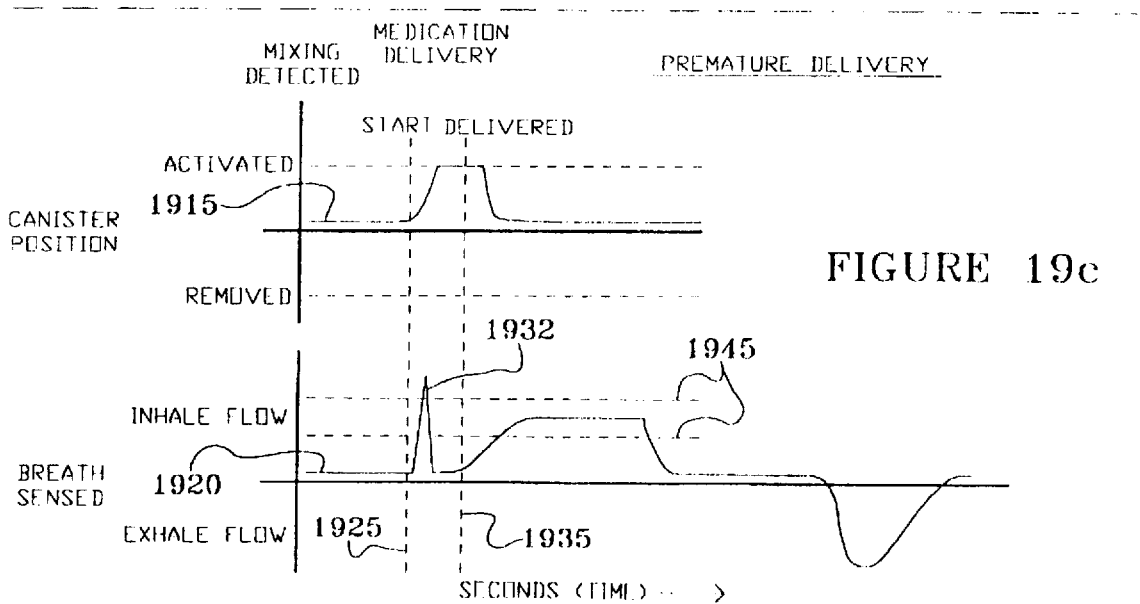
Figures 19D, 19E:
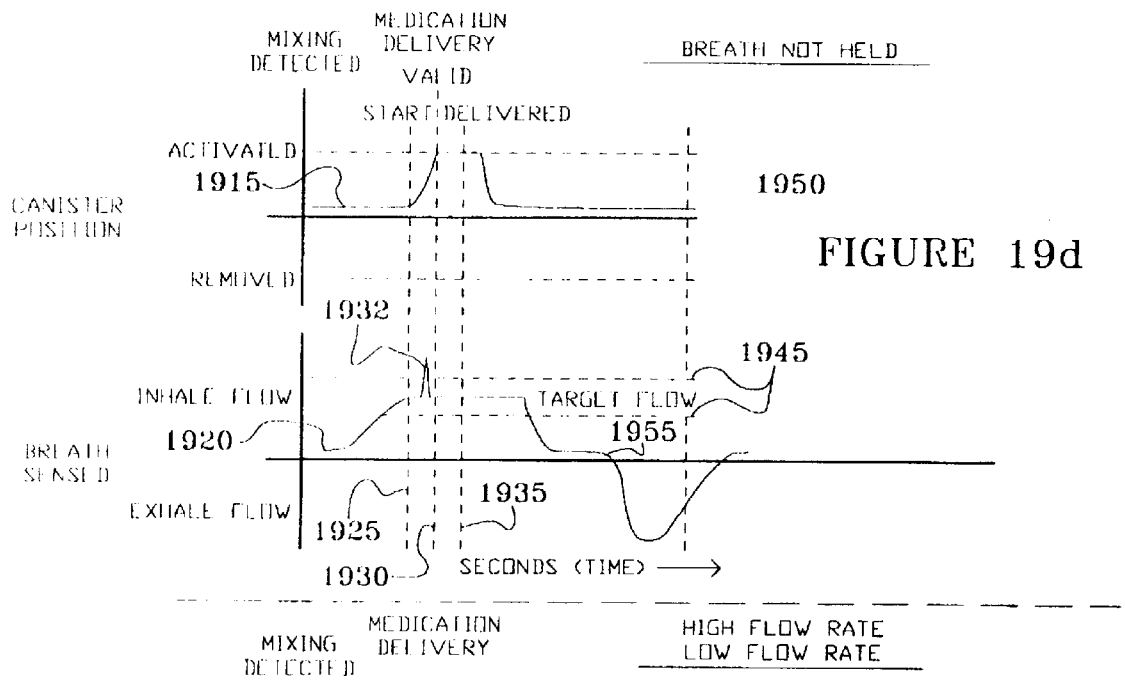

FIGS. 19c, 19d and 19e show the result of wave forms 1915 and 1920 from incorrect or improper sequencing of the use of the MDI improved apparatus 100. In FIG. 19c, a premature delivery is shown, where the start 1925 of medication delivery has indicated, and even was delivered 1935 prior to the user/patient achieving the target flow 1945 inhalation rate. The medication in this sequencing as shown in FIG. 19c of the apparatus 100, would have landed on the patient's tongue, dissolved and would be swallowed. Very little of the medication would have made its way to the respiratory system.

The sequence shown in FIG. 19d, indicates that the user/patient achieved a proper target flow 1945 inhalation rate prior to the start 1925, valid 1930 and medication delivered 1935 (before releasing canister) and also did continue to inhale long enough to receive the delivered medication into the respiratory system. But the patient did not hold breath 1955 long enough (to the exhale OK 1950 dotted line time). The curve indicated an exhalation occurred, on wave form 1920, almost immediately after inhalation. Such a sequence would cause most of the medication to be expelled out in the exhalation prior to it dissolving in the respiratory system of the patient.

In FIG. 19e, it is illustrated a correct timing of sequencing, but the user/patient inhaled either too hard or too fast, as indicated at 1960 in the over target flow 1945 inhalation rate; or too soft or too slow, as indicated at 1965 in the under target flow 1945 inhalation rate. In the case of the too hard or too fast 1960 (over target flow inhalation rate) the majority of medication would land on the back of the patient's throat, dissolve and be swallowed instead of making its way to the respiratory system. Likewise, in the case of the too soft or too slow 1965 (under target flow inhalation rate) the majority of medication would land on the patient's tongue, and again would dissolve and be swallowed instead of being received into the respiratory system of the patient.

In FIG. 20 is shown the accessory chronolog 1200 attached to a commercial vial/actuator combination 1220 via the adaptable housing 1210 comprising the present invention apparatus 100 which illustrates the various data communications. The dotted lines 2010 indicate where the apparatus 100 is placed in a cradle 2020 of the docking station 2030. Note the front panel 1410 of the accessory chronolog 1200 (as shown in FIG. 14) is facing the cradle 2020 so that the IR transmitter 1450 and IR receiver 1460 are aligned with reciprocal IR transmitter and receiver located in the docking station 2030. The design of the cradle 2020 is such that the apparatus 100 can only fit with a proper alignment. The function of data transfer is automatic and is accomplished by wireless IR digital technique. It is important to understand that there is no physical electrical connection between the apparatus 100 and the docking station 2030. The communications is wireless, allowing this function to be as easy to accomplish, for example, as the act of putting a telephone hand set down into its cradle on top of a telephone.

Any usage of the apparatus 100 that was recorded in its memory is uploaded to the docking station 2030 memory, and any up-dated instructions issued by the physician are down-loaded from the docking station memory to the apparatus 100. The transfer of data/information shall only take a few seconds, depending on amount of stored data. The apparatus 100 may be removed at completion of transfer and the data is retained in the docking station 2030 memory for retrieval.

The docking station has the means to connect to a telephone line via a conventional line jack. The internal modem allows the docking station 2030 to be accessed remotely via telephone company lines 2040 by a conventional personal computer (PC) 2050, or to initiate a call to the remote PC 2050 for data transfer interlink. The PC 2050 is operating a software program suitable for the retrieval of acquired apparatus 100 data temporarily stored in the docking station 2030 memory. The PC 2050 software program can also down-load new patient instructions to the docking station 2030 memory where it is temporarily stored until the next occasion the apparatus 100 is placed in the cradle 2020.

It is explicitly understood that a plurality of electronically controlled peripheral devices, for delivering medication such as the apparatus 100 of the present invention, may communicate with the docking station 2030 to transfer data/information. This affords a user/patient which may have more than one medication drug to be properly monitored with respect to compliance in the prescribed regime. The docking station 2030 and PC 2050 can distinguish between data/information of each said electronically-controlled peripheral device apparatus 100 by two identifying means; 1) an electronic serial number and, 2) the user/patients name with medication type. These identification means are transferred along with any data/information at every communications between apparatus 100 and docking station 2030, and between docking station 2030 and remote PC 2050.

In operation the improved accessory chronolog 1200 of the alternative embodiment of the present invention, being adaptable to any of the conventional commercially available vial/actuator combinations 1220, making an improved apparatus 100 which allows the originally manufactured, tested and FDA approved and authorized actuators fitted for monitoring the user/patient for proper usage and compliance without interfering with, or altering, the delivery of medication. The apparatus 1200 by means of an accelerometer and reed switch, generates a mixing detect 1910 signal properly indicating that the pharmaceutical manufacturer's recommendation for pre-mixing the medication has occurred prior to inhalation of said medication. That a strain gauge dynamic sensing arm 1555 indicated that a vial/ canister 1590 is received into the commercial actuator 1575 and is properly seated into its aerosol chamber 1720 and ready for use, and, that it can detect the start 1925 and valid 1930 actuation 1940 of the medication delivery process. That an air flow fast response thermistor 1560 can detect the proper inhalation sequence in the medication delivery, as the user/patient inhales through the mouthpiece 1585, a portion of air would enter air inlet 1440 in housing 1510 (of apparatus 1200) passing through air channel 1561 (which is outside the gasket 1545 area) and the hole in the main-PCB 1540. As it passes through the hole in the main-PCB, the air will pass over the very small fast response thermistor 1560 and continues through the access hole 1260 that is shared with the dynamic sensing arm 1555. This fraction of inhaled air is representative of the remainder of air drawn into the actuator 1575 around the sides of the vial/canister 1590. The perturbation of air flow producing the medication discharge signal 1932 indicates positively that a metered dose of medication inhalant has been released from the vial/canister and is available for inhalation. With any exhalation by the patient, exhaled air would reverse the above-indicated path, allowing a fraction out the access hole 1260 and through the main-PCB over the thermistor 1560 and through the air channel 1561 and expelled out the inlet holes 1440.

The generated signals (each may be recorded) will document that a user/patient has complied with all pharmaceutical manufacturer's recommendations as well as the prescribing physician's instructions, resulting in data indicative that medication has positively been dispensed in the user/patient's mouth, throat and respiratory system after being properly mixed. Any deviation from a correct usage, indicating for example: medication not mixed enough, vial/canister not properly seated, premature delivery, delayed delivery, not inhaling long enough, not holding breath long enough, inhaling too hard or too fast, or too soft or too slow, resulting in the medication either landing and dissolving on the back of the throat or on the tongue of the patient instead of being received into the respiratory system where it is intended.

All such events and maneuvers are either displayed on the LCD display 1535 and/or indicated on the piezo transducer 1520 audibly for immediate feedback to the user/patient. Further, the events are time-stamped and recorded in the device memory system for retrieval at some later time. The system of the present invention can record for as long as six months, depending on preprogrammed configuration. There are infrared (IR) transmitting and receiving elements 1450 and 1460 to wirelessly communicate (short range) with either peripheral support devices or directly to a personal computer for the up-loading of stored memory data. The retrieved information is an exact user/patient "mapping" as to the performance of medication being delivered from improved apparatus 100. The physician or researcher may determine, for example, only 70% of the drug was successfully received into the respiratory system at only 50% of the time and a proper correlation as to compliance to prescribed therapeutic regime to a drug's effectiveness can quickly be ascertained by such chronologged retrieved and analyzed information.

It is important to understand that the microprocessor 605 indicated in FIG. 8, controlling the electronic components therein of the previous embodiments, can perform the tasks of the improved present invention in the accessory chronolog apparatus 1200. Also, the concept of an adaptable housing 1210 may be manufactured into the pharmaceutical company produced commercial actuator 1575, by the pharmaceutical manufacturer. Such a concept would allow the accessory chronolog apparatus 1200 to "snap" directly onto the pharmaceutical manufactured actuator with out any need for the punching of the access hole 1260. The focus here is that the actuator 1575, being relatively inexpensive to produce (after it has been FDA approved and authorized), may be easily replaced by snapping off the apparatus 1200 and placing it onto a new actuator as necessary be from time to time because it wore out or for sanitary reasons.

Anyone skilled in the art of electronic design, microprocessor programming, mechanical design and manufacturing can achieve the art being taught in the present invention. Further, although the preferred embodiment is greatly detailed, other configurations in either style or component technologies may result in a similar accessory chronolog apparatus 1200. While the invention has been particularly described and illustrated in detail with reference to the preferred embodiments, it should be understood by those skilled in the art that equivalent changes in form and detail may be made without departing from the true spirit and scope of the invention as claimed, except as precluded by the prior art. The embodiments of the invention for which an exclusive privilege and property right is claimed are defined as follows:

The embodiments of the invention for which an exclusive and property right is claimed are defined as follows:

1. An accessory chronolog apparatus adapted for attachment to a conventional pressurized inhalant package, the package includes an actuator housing with one end having a mouthpiece and an opposite end having an opening for receiving a vial/canister therein, the vial/canister having a valve stem used for dispensing a prescribed dosage of medication inhalant in an aerosol chamber inside the actuator housing, the aerosol chamber is disposed next to an outlet of the mouthpiece, the actuator housing having a hole in a side thereof, the accessory chronolog apparatus comprising:

a chronolog housing;

processing means including a processor disposed in said chronolog housing, said chronolog housing adapted for attachment to the actuator housing, said processing means for logging when the medication inhalant is released from the vial/canister;

a strain gauge sensing arm, one end of said sensing arm in electrical communication with said processing means, an opposite end of said sensing arm adapted for receipt through the hole in the side of the actuator end of the vial/canister, said sensing arm sensing and signaling said processing means when the vial/canister is properly depressed for release of medication; and a fast response thermistor mounted inside said chronolog housing and in an air flow path between the hole and the side of the actuator housing and an opening in said chronolog housing, said thermistor in electrical communication with said processing means, said thermistor sensing and signaling said processing means each occurrence an amount of inhale air flow in the actuator housing.

2. The accessory chronolog apparatus as described in claim 1, further including a medication mixing sensor in electrical communication with said processing means, said mixing sensor disposed in said chronolog housing, said mixing sensor for sensing and signaling said processing means when proper mixing of the medication in the vial/canister has occurred.

3. The accessory chronolog apparatus as described in claim 2, wherein said medication mixing sensor is an accelerometer sensor and reed switch, when the medication in the vial/canister is properly shaken, the accelerometer sensor closes the reed switch and the processing means is signaled that proper mixing has occurred.

4. The accessory chronolog apparatus as described in claim 3 wherein said accelerometer sensor is a spring biased magnet, when said magnet is compressed against the spring, the magnet's magnetic field comes in contact with and closes said reed switch.

5. The accessory chronolog apparatus as described in claim 1, wherein said fast response thermistor senses and signals said processing means when medication is released from the vial/canister.

6. The accessory chronolog apparatus as described in claim 5, wherein when the medication is discharged from the vial/canister, an instantaneous pressure change creates a perturbance in the ambient air, the perturbance of air sensed by said fast response thermistor for signaling said processing means.

7. The accessory chronolog apparatus as described in claim 1, further including display means in electrical communication with said processing means and disposed on said chronolog housing, said display means for displaying when the vial/canister is engaged and disengaged inside the actuator housing, for displaying when the inhalant is released from the vial/canister, for displaying the amount of inhalant dispensed from the vial/canister and the duration of the inhalant dispensed, for displaying each occurrence of inhale flow in the actuator housing and for displaying the amount of inhale flow in the actuator housing.

* * * * *